(12) United States Patent
Kim et al.

(10) Patent No.: US 7,413,858 B2
(45) Date of Patent: Aug. 19, 2008

(54) **IDENTIFICATION METHOD OF GENUS *STREPTOMYCES* BY USING *GROEL2* GENE**

(75) Inventors: Bum-Joon Kim, Seoul (KR); Chang-Jin Kim, Daejeon (KR); Young Hwan Ko, Jeju-do (KR); Jeong-Sam Koh, Jeju-do (KR); Dong-Jin Park, Daejeon (KR); Hyang Burm Lee, Daejeon (KR); Hong Kim, Seoul (KR); Sun-hyun Kim, Seoul (KR)

(73) Assignee: Korea Research Institute of Bioscience and Biotechnology, Daejon (KR)

( * ) Notice: Subject to any disclaimer, the term of this patent is extended or adjusted under 35 U.S.C. 154(b) by 257 days.

(21) Appl. No.: 10/824,527

(22) Filed: Apr. 15, 2004

(65) Prior Publication Data

US 2004/0265873 A1 Dec. 30, 2004

(30) Foreign Application Priority Data

Apr. 18, 2003 (KR) .................... 10-2003-0024656
Nov. 14, 2003 (KR) .................... 10-2003-0080580

(51) Int. Cl.
*C12Q 1/68* (2006.01)
*C12P 19/34* (2006.01)
*C07H 21/02* (2006.01)
*C07H 21/04* (2006.01)

(52) U.S. Cl. ................ 435/6; 536/23.1; 536/24.3; 435/91.2

(58) Field of Classification Search ................ None
See application file for complete search history.

(56) References Cited

U.S. PATENT DOCUMENTS 5,474,796 A * 12/1995 Brennan ................ 427/2.13
5,631,130 A * 5/1997 Leckie et al. ................ 435/6

OTHER PUBLICATIONS

Tokunaga et al; Microbiology and Immunology, 1992, 36 pp. 55-66.*
Merz, et al; European Journal of Plant Pathology, vol. 11, p. 371-379, 2005.*
Genbank Accession No. M76658.*
GenBank Accession No. M76658 1993.*
Annaliesa S. Anderson, et al.; "The Taxonomy of *Streptomyces* and Related Genera", International Journal of Systematic and Evolutionary Microbiology, 51(3), 797-814, (2001).
Elizabeth A.B. Emmert et al.; "Biocontrol of Plant Disease: A (Gram-) Positive Perspective", FEMS Microbiology Letters, 171(1), pp. 1-9, (1999).
Jens Nielsen; "Metabolic Engineering: Techniques for Analysis of Targets for Genetic Manipulations", Biotechnology and Bioengineering, 58(2-3), pp. 125-132, (1998).
C.R. Hutchinson et al.; "Genetic Engineering of Doxorubicin Production in *Streptomyces peucetius*: A Review", Journal of Industrial Microbiology & Biotechnology, 23(1), pp. 647-652, (1999).
Kumiko UEDA et al.; "Two Distinct Mechanisms Cause Heterogeneity of 16S rRNA", Journal of Bacteriology, 181(1), pp. 78-82, (1999).
V.B.D. Skerman et al.; "Approved Lists of Bacterial Names", International Journal of Systematic Bacteriology, 30, pp. 225-420, (1980).

* cited by examiner

*Primary Examiner*—Jehanne S Sitton
(74) *Attorney, Agent, or Firm*—Finnegan, Henderson, Farabow, Garrett & Dunner, L.L.P.

(57) ABSTRACT

Disclosed is a method for identifying *Streptomyces* species using groEL2 gene that can compensate for drawbacks of conventional methods of morphologic classification and 16S rDNA identification being time-consuming, unfaithful, and expensive, thus enabling to efficiently identify *Streptomyces* species.

12 Claims, 6 Drawing Sheets

M: ΦX174 DNA Size Marker, 1: *S. aculeolatus*, 2: *S. albireticuli*

3: *S. alofaciens*, 4: *S. albus*, 5: *S. aminophilus*

6: *S. argenteolus*, 7: *S. carpinesis*, 8: *S. chartreuses*

9: *S.cinnamonesis*, 10: *S.coeruleorubidus*, 11: *S. diastaticus*

12: *S. erumpens*, 13: *S. griseolus*, 14: *S. hygroscopicus*

15: *R. equi*, 16: *T. paurometbola*

M: DNA Size Marker consisting of DNA fragments of ΦX174 digested with HaeIII

1: S. scabiei ATCC 49173$^T$

2: S. scabiei DSMZ 40962

3: S. acidiscabies ATCC 49003$^T$

4: S. turgidiscabies ATCC 700248$^T$

5: Kangwon-S20, 6: Kangwon-S53, 7: Jeju-H11, 8: Jeju-H 20

Scale: each − is approximately equal to the distance of 0.617934

★: Non type strain T: Type reference strain

IDENTIFICATION METHOD OF GENUS *STREPTOMYCES* BY USING *GROEL2* GENE

FIELD OF THE INVENTION

The present invention relates to a method for identifying genus *Streptomyces* using groEL2 gene which comprises the steps of preparing a specific primer capable of amplifying groEL2 gene of all *Streptomyces* species; amplifying groEL2 gene using the primer; sequencing the nucleotide sequence of an amplified product to build a database; and identifying unknown *Streptomyces* species using the database.

BACKGROUND OF THE INVENTION

Due to the developments of methods for isolating and purifying natural products, more than 10,000 kinds of antibiotics have been isolated from microorganisms. Further, continued studies on a new identification method and technology, discovery of new isolation resources and application of microbial metabolites to veterinary and agricultural industries have contributed to the development of antibiotics using microorganisms.

Since mutual antagonism between microorganisms was first observed by Tyndall, various antibiotics have been actively developed. For example, actinomycin was isolated from *S. antibioticus* by Waksman and Woodruff, and streptomycin, from *S. griseus* by Schatz and Wakman based on the discovery of penicillin by Fleming in 1929. As actinomycin and streptomycin were used for treating pulmonary tuberculosis, *Streptomyces* has been regarded as an important microorganism for producing antibiotics in the fields of industry and medical sciences. Since metabolites of *Streptomyces* are very diverse, it can produce various kinds of biologically active substances. Among 10,000 kinds of biologically active substances investigated from microorganisms until now, about two-thirds are found in *Streptomyces*. Accordingly, the importance of *Streptomyces* in investigating biologically active substance has been much emphasized. *Streptomyces* has been regarded as one of the most important microorganisms in biomaterial industry.

*Streptomyces* is one of the most diverse microbial species and possesses many different biologically metabolic activities even in the same species (Anderson A S, Wellington E M. The taxonomy of *Streptomyces* and related genera. *Int. J. Syst. Evol. Microbiol.* 2001, 51(3): 797-814). Accordingly, numerous biologically active substances have been developed from *Streptomyces*'s metabolites, and infinite possibilities of these substances for applying to agricultural and marine industries (breeding, extermination of damages by blight and harmful insects), environmental industry (disposal of wastes), fine chemical industry (technochemical medicines), food industry (raw materials, additives), semiconductor industry (biosensors) and medicine have been suggested.

There have been conducted numerous studies using natural products for the purpose of preventing, alleviating or treating diseases (Emmert E A, Handelsman J. Biocontrol of plant disease: a (Gram–) positive perspective. *FEMS Microbiol. Lett.* 1999, 1; 171(1): 1-9; Nielsen J. Metabolic engineering: techniques for analysis of targets for genetic manipulations. *Biotechnol. Bioeng.* 1998, 58(2-3): 125-32; Hutchinson C, Colombo A. Genetic engineering of doxorubicin production in *Streptomyces peucetius*: *J. Ind. Microbiol. Biotechnol.* 1999, July; 23(1): 647-652). One of such methods for approaching the purpose is to secure various biological resources. Considering the importance of *Streptomyces* in biological diversity and industrialization possibility, it is expected to play an important role in practical applicability.

The international agreement to biological diversity relates to preservation of biological diversity, prolonged utilization and fair distribution of profits obtained from the existing genetic resources, and is interested in the preservation of worldwide biological resources. At the point of becoming worse environmental pollution, it has been regarded as an important matter to secure and prevent domestic microbial resources. The United States has approved a patent right for a microorganism since 1980 and the microorganism has become the subject matter of patent since 1987 in the country.

For obtaining a patent right for a microorganism, it is important to analyze exactly the phylogenetical classification of a target microorganism as well as the characteristics of biologically active compounds produced by the microorganism.

The current method for screening a new compound from *Streptomyces* has been conducted for the purpose of finding a new compound, but it h as often resulted in finding only already patented compounds. Accordingly, it is preferable to carry out the screening of a new compound after a new species or a new strain of *Streptomyces* is identified, thereby increasing the possibility of discovering new compounds. The classification of *Streptomyces* has been based on a numerical taxonomy via physiological, morphological or biochemical analyses according to the previously discovered phenotypic features.

However, there are several obstacles in conducting the numerical taxonomy for *Streptomyces*: exact identification of *Streptomyces* requires too much time because there are too many subtypes in *Streptomyces*; *Streptomyces* has an extremely slow growth rate [cell cycle of *E. coli* (20 min); cell cycle of *Streptomyces* (2-3 hrs)]; and its analytical result is not very reliable.

Recently, the numerical taxonomy has been replaced by a molecular taxonomy, which determines a species by analyzing a chronometer molecule showing all bacterial phylogenetic relationship via analyses of nucleotide sequences. Among the chronometer molecules, 16S rDNA molecule has been widely employed for the identification of a microorganism, in particular, *Streptomyces*.

The method for identifying a microorganism by sequencing analysis of 16S rDNA has been widely employed in place of the numerical taxonomy using the previous phenotypic features. Further, 16S rDNA has also been employed as a target gene of a kit for detecting a microorganism including pathogenic bacteria by a molecular method (e.g., a gene probing kit for detecting a *mycobacterium*).

However, there are several drawbacks in the method using 16S rDNA as follows. Although a hypervariable region showing various sequence mutations exists in 16S rDNA, the full-length of 1.5 kb 16S rDNA must be sequenced for the exact identification of a microorganism by comparative sequencing analysis, which is time-consuming and cost-ineffective. This problem raises the problem that too many oligomers should be used to develop a method for identifying a microorganism by a DNA chip in the future. Further, it requires much expense for analyzing the data of 450 kinds or more of species including *Streptomyces*. Accordingly, while 16S rDNA database of other strains are established at Genbank, that of total *Streptomyces* species has not been completed except a few species. Besides, it has been reported that 16S rDNA exists in the form of a multi-copy gene in entire chromosomes in some *Streptomyces* species and the nucleotide sequences of these alleles are different from each other, which becomes a critical defect for the identification method using 16S rDNA (Ueda K, Seki T, Kudo T, Yoshida T, Kataoka M. Two distinct mechanisms cause heterogeneity of 16S rRNA. *J. Bacteriol.* 1999, January; 181(1): 78-82). Namely, several nucleotide sequences of 16S rDNA exist in one strain, and this raises a technical problem in sequencing analysis. Because it is not possible to directly analyze the nucleotide sequence of a PCR product after PCR amplification of the target gene of *Streptomyces*, the amplified product must be cloned into a vector and several clones thus obtained are subjected to sequencing analysis.

Due to these problems, it is necessary to select a new chronometer molecule besides 16S rDNA for the identification of *Streptomyces*.

Potato scab is a pathogenic disease caused by three different *Streptomyces* species of *S. scabiei, S. acidiscabies* and *S. turgidiscabies*, with rare exceptions of a few *Streptomyces* species. Of them, *S. scabiei* is the major pathogenic microorganism which is composed of many genetical side groups.

Since *Streptomyces* is the most diverse species with a relatively slow growth rate as compared to other microorganisms, it is very difficult to classify *Streptomyces* species by a biochemical or physiological method (Skerman, V. B. D., McGowan, V., Sneath, P. H. A. (ed): Approved Lists of Bacterial Names. *Int. J. Syst. Bacteriol.* 1980, 30: 225-420). Therefore, several methods, e.g., a fatty acid analyzing method, DNA-DNA hybridization method and 16S rRNA gene analyzing method, have been developed for identifying a potato scab pathogenic microorganism. Of these methods, the method for analyzing 16S rRNA has an advantage in defining a phylogenetic relationship between microorganisms or identifying an unknown strain and has been effectively used for identifying pathogenic bacteria. However, it is very difficult to exactly classify bacterial strains showing close phylogenetic relationship among them because the nucleotide sequence of 16S rRNA is highly conserved in these strains. Accordingly, there is a need of establishing a method for identifying a potato scab pathogenic microorganism using a new substitute gene for 16S rRNA. To compensate the defect of 16S rRNA analyzing method, there was developed a method for identifying an unknown strain using 16S-23S ITS region as a target gene, a region known to be more hypervariable than 16S rDNA. However, this method is not suitable for the classification and identification of a potato scab pathogenic microorganism because 16S-23S ITS target gene has a few different nucleotide sequences in each individual. Therefore, it has been a long-awaited need to develop a method for identifying a potato scab pathogenic microorganism using a new chronometer molecule as a target gene.

The present inventors have therefore endeavored to find a method that meets the above need, and developed a method for identifying *Streptomyces* species using groEL2 gene which comprises the steps of preparing a specific primer for groEL2 gene conserved in all *Streptomyces* species; amplifying groEL2 gene using the primer; sequencing the nucleotide sequence of amplified product to build a database; and identifying unknown *Streptomyces* species using the database.

SUMMARY OF THE INVENTION

Accordingly, an object of the present invention is to provide a method for identifying *Streptomyces* using groEL2 gene which comprises the steps of preparing a specific primer for groEL2 gene which is capable of amplifying groEL2 gene of all *Streptomyces* species; amplifying groEL2 gene using the primer; sequencing the nucleotide sequence of an amplified product to build a database; and identifying unknown *Streptomyces* species using the database.

It is a further object of the present invention to provide a method for identifying a potato scab pathogenic microorganism using the method.

In accordance with one aspect of the present invention, there is provided a specific primer capable of amplifying groEL2 gene, which is conserved in all *Streptomyces* species; a groEL2 gene fragment amplified from *Streptomyces*; and a groEL2 gene fragment amplified from a potato scab pathogenic microorganism.

In accordance with another aspect of the present invention, there is provided a method for identifying *Streptomyces* species, which comprises the steps of amplifying groEL2 gene using the primer, sequencing the amplified product to build a database, and identifying unknown *Streptomyces* species using the database.

It is still another object of this invention to provide a method for identifying a potato scab pathogenic microorganism from *Streptomyces* species.

BRIEF DESCRIPTION OF THE DRAWINGS

The above and other objects and features of the present invention will become apparent from the following description of the invention, when taken in conjunction with the accompanying drawings which respectively show; wherein.

DETAILED DESCRIPTION OF THE INVENTION

Figure 1:
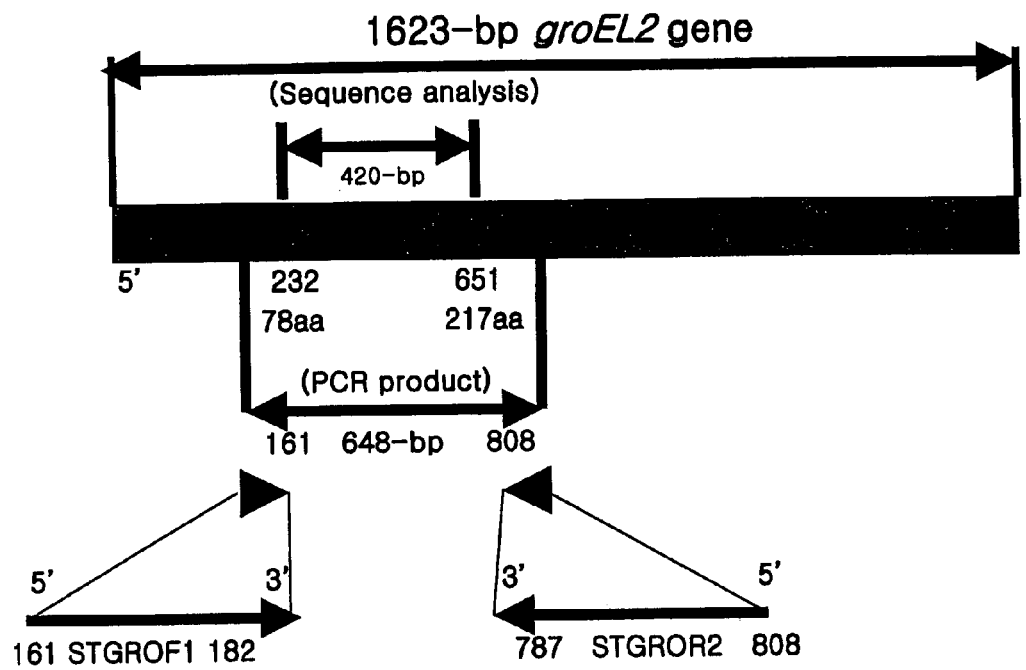
FIG. 1 shows the recognition sites of groEL2 specific primers and groEL2 gene fragment amplified using the primers.

The present invention provides a specific primer capable of amplifying groEL2 gene which is conserved in all *Streptomyces* species; a groEL2 gene fragment of *Streptomyces* amplified by using the primer; and a groEL2 gene fragment of a potato scab pathogenic microorganism amplified by using the primer.

The present invention also provides a method for identifying *Streptomyces* species, which comprises amplifying groEL2 gene using the primer, sequencing the nucleotide sequence of an amplified product to build a database, and identifying unknown *Streptomyces* species using the database.

Further, the present invention provides a method for identifying a potato scab pathogenic microorganism from *Streptomyces* species.

The present invention is described in detail hereunder.

In one aspect, the present invention relates to an identification method of genus *Streptomyces* by using groEL2 gene which comprises the steps of preparing a specific primer for groEL2 gene conserved in all *Streptomyces* species; amplifying groEL2 gene using the primer; sequencing the nucleotide sequence of an amplified product to build a database; and identifying *Streptomyces* species using the database.

The present invention has employed groEL2 gene encoding groEL2 protein as a new chronometer molecule substitute for 16S rDNA for identifying *Streptomyces* species. groEL2 gene encodes a stress-related protein in bacteria whose function is well conserved both in human and bacteria. Accordingly, groEL2 gene can be regarded as a chronometer molecule that a gene mutation reflects random change involved in cell cycle rather than external selective stress. Namely, it has been thought that the nucleotide sequence of groEL2 gene represents a phylogenic relationship among microorganisms.

groEL2 gene employed as a chronometer molecule in the present invention has advantages over the previously employed 16S rDNA as follows:

1. In order to exactly identify a bacterial strain by a comparative sequencing analysis using 16S rDNA as a target gene, almost 1.5-kbp of the full-length gene must be sequenced. However, it is possible to precisely identify a bacterial strain by analyzing the nucleotide sequence of only 420-bp or 423-bp of groEL2 gene fragment. This difference can curtail the cost for identifying a bacterial strain several folds.

2. The most critical problem of 16S rDNA analyzing method for identifying *Streptomyces* species is that it is impossible to analyze *Streptomyces* species using a direct nucleotide sequencing method since 16S rDNA exists as a multi-copy gene in one individual in some *Streptomyces* species and the multi-copy gene may have different nucleotide sequences. In this case, the nucleotide sequence of 16S rDNA must be indirectly sequenced after a cloning procedure, which leads to several folds higher waste in labor, time and cost than that of a direct nucleotide sequencing method. However, the identification method using groEL2 gene can make up for this defect because it has been reported that groEL2 gene has a single nucleotide sequence in each individual.

3. 16S rDNA has hypervariable regions in different lengths, which suggests the presence of a gap in a nucleotide sequence alignment. However, groEL2 gene has an only 420-bp of nucleotide sequence fragment in almost all *Streptomyces* species except a few species. The exceptional species also have a 423-bp of nucleotide sequence fragment wherein only one amino acid, i.e., 3-bp nucleotides, is added. Accordingly, this feature functions as an advantage in a nucleotide sequence alignment or a determination of nucleotide sequence.

4. 16S rDNA is not a structural gene, and therefore, does not encode a functional polypeptide. Accordingly, the identification method using 16S rDNA cannot employ the amino acid sequence of the polypeptide encoded by 16S rDNA for identifying a bacterial strain. However, since a functional gene, groEL2, encodes a polypeptide, it is capable of employing not only the nucleotide sequence of groEL2 fragment but also the amino acid sequence of groEL2 protein encoded thereby for identifying a bacterial strain.

5. There is a problem of building an individual database of 16S rDNA because the nucleotide sequencing analysis of *Streptomyces* species using 16S rDNA has been sporadically carried out by several different researchers since the middle of 1980. However, since it was discovered that all nucleotide sequence of groEL2 gene analyzed in the present invention is new in Genbank, groEL2 gene has the advantage of building an individual database for classifying *Streptomyces* species. Further, the inventive groEL2 gene has the advantages over rpoB gene disclosed in Korea Patent Laid-open Publication No: 2003-15124 that groEL2 gene shows more variable mutations in the nucleotide sequence and amino acid sequence encoded thereby between two *Streptomyces* species, and therefore, is more favorable as a chronometer molecule for classifying and diagnosing *Streptomyces* species.

The inventive method for identifying genus *Streptomyces* by using groEL2 gene is described as follows.

The identification method of the present invention comprises the steps of 1) preparing a specific primer capable of amplifying groEL2 gene of all *Streptomyces* species and amplifying groEL2 gene of target strain using the primer;
2) analyzing the nucleotide sequence of an amplified product; and
3) comparing thus obtained nucleotide sequence with that of a reference strain.

In Step 1), to prepare a specific primer for *Streptomyces* species to amplify groEL2 gene, the full-length nucleotide sequences of *S. lividans* and *S. albus* derived groEL2 genes were compared with that of *T. paurometabola* derived groEL2 gene which is phylogenetically close to *Streptomyces* species, and the most highly conserved regions were selected as the recognition sites for forward and reverse primers, respectively. Then, 40 reference strains of *Streptomyces* species were subjected to PCR amplification using the primer pair to confirm whether 648-bp of PCR products are amplified in all target strains.

Preferably, the primer has the nucleotide sequence of SEQ ID NO: 1 or SEQ ID NO: 2.

A target strain was subjected to PCR using the *Streptomyces* specific primers to amplify groEL2 gene, and then, the nucleotide sequence of the amplified groEL2 gene fragment was analyzed. At this time, the nucleotide sequence database of groEL2 gene fragments of reference strains comprises the nucleotide sequences of SEQ ID NOs: 3 to 42.

When the groEL2 nucleotide sequences of reference and target strains are analyzed and the target strain is determined as a relevant strain by comparing their nucleotide sequences, the nucleotide sequence of a target strain to be subjected to identification was analyzed and added to an alignment database. Then, the nucleotide sequence alignment was carried out again to complete a phylogenetic tree, which resulted in forming a branch close to a relevant strain and determining a species of a target strain from the phylogenetic tree. Further, it was possible to identify a strain to examine whether the target strain shows a 99.8% sequence homology compared with a reference strain. It is due to the fact that the nucleotide sequence variation in same species does not exceed 0.2%.

To verify whether the groEL2 database of *Streptomyces* species build in is the present invention is applicable to identify an unknown strain in practice, 5 non-reference strains were subjected to identification by sequencing the groEL2 gene fragment and comparing the nucleotide sequence with that of a reference strain. As a result, it was found that 3 non-reference strains of *S. hygroscopicus* (KCTC 9030, KCTC 9031 and KCTC 9069) had 100%, 99.8% and 99.8% of a sequence homology, respectively, and were located at a position close to a reference strain of *S. hygroscopicus* (KCTC 9782) in the phylogenetic tree. It was also found that 2 non-reference strains of *S. albus* (KCTC 1136 and KCTC 1533) had 99.8% and 100% of a sequence homology, respectively, and were located at a position corresponding to a reference strain of *S. albus* (KCTC 1082) (see FIG. 6). In conclusion, it is important for a chronometer molecule used for the identification of a bacterial strain to have features of intraspecies conservation as well as interspecies variation. The interspecies variation of groEL2 gene has been described above, and the intraspecies conservation of groEL2 gene has been proved by analyzing the nucleotide sequences of 5 non-reference strains. When the nucleotide sequences of 5 non-reference strains were compared with that of a reference strain, they showed a sequence homology ranging from 99.8% to 100%. Further, all 5 non-reference strains can be identified by comparative nucleotide sequence analysis.

Meanwhile, the present invention provides a method for identifying a potato scab pathogenic microorganism from *Streptomyces* species, which comprises:

1) amplifying a groEL2 gene fragment of a target strain by using a specific primer for groEL2 gene of *Streptomyces* species;

2) analyzing the nucleotide sequence of groEL2 gene fragment; and 3) comparing the nucleotide sequence with that of groEL2 gene fragment of a reference strain causing potato scab.

15 reference strains to be identified that are well-known as potato scab pathogenic microorganisms were subjected to PCR using the primer to examine whether 648-bp of PCR product is amplified in all strains.

A target strain was subjected to PCR using the *Streptomyces* specific primer to amplify groEL2 gene, and then, the nucleotide sequence of the amplified groEL2 gene fragment was analyzed. At this time, the nucleotide sequence database of groEL2 gene fragments of reference strains comprised the nucleotide sequences of SEQ ID NOs: 43 to 61.

15 reference strains causing potato scab and 20 isolated strains obtained from Kangwon-do and Jeju-do derived potato scab pathogenic tissues were subjected to sequencing analysis. As a result of comparing the nucleotide sequences of 15 reference strains by multi-alignment, it was found that three strains of *S. scabiei*, *S. acidiscabies* and *S. turgidiscabies* have different nucleotide sequences from each other and belong to a different group in a phylogenetic tree, respectively.

Accordingly, the inventive identification method solves the problems of the previous conventional classification based on the morphological and biochemical tests and 16S rDNA identification method (time-consuming, incorrectness, cost-ineffective, etc.), and therefore, can be effectively used for identifying *Streptomyces* species.

This invention is explained in more detail based on the following Examples but they should not be construed as limiting the scope of this invention.

REFERENCE EXAMPLE 1

40 reference strains consisting of 38 *Streptomyces* strains, 1 *Rhodococcus* strain and 1 *Tsukamurella* strain were obtained from Korean Collection for Type Cultures (KCTC) of Korea Research Institute of Bioscience and Biotechnology (KRIBB), and subjected to sequencing analysis of groEL2 gene. Further, total 5 non-reference strains of 2 species (*S. hygroscopicus* and *S. albus*) were subjected to comparative analysis of the nucleotide sequence of groEL2 gene (Table 1).

TABLE 1

| No | Name | Source |
|---|---|---|
| Reference Strain of *Streptomyces* | | |
| 1 | *S. acrimycini* | KCTC 9679$^T$ |
| 2 | *S. aculeolatus* | KCTC 9680$^T$ |
| 3 | *S. alanosinicus* | KCTC 9683$^T$ |
| 4 | *S. albireticuli* | KCTC 9744$^T$ |
| 5 | *S. albofaciens* | KCTC 9686$^T$ |
| 6 | *S. albogriseolus* | KCTC 9675$^T$ |
| 7 | *S. alboniger* | KCTC 9014$^T$ |
| 8 | *S. albus* | KCTC 1082$^T$ |
| 9 | *S. ambofaciens* | KCTC 9111$^T$ |
| 10 | *S. aminophilus* | KCTC 9673$^T$ |
| 11 | *S. anandii* | KCTC 9687$^T$ |
| 12 | *S. argenteolus* | KCTC 9695$^T$ |
| 13 | *S. bambergiensis* | KCTC 9019$^T$ |
| 14 | *S. capillispiralis* | KCTC 1719$^T$ |
| 15 | *S. carpinesis* | KCTC 9128$^T$ |
| 16 | *S. catenulae* | KCTC 9223$^T$ |
| 17 | *S. cellulosae* | KCTC 9703$^T$ |
| 18 | *S. chartreusis* | KCTC 9704$^T$ |
| 19 | *S. chattanoogensis* | KCTC 1087$^T$ |
| 20 | *S. cinnamonensis* | KCTC 9708$^T$ |
| 21 | *S. cinereoruber* | KCTC 9707$^T$ |
| 22 | *S. cirratus* | KCTC 9709$^T$ |
| 23 | *S. coeruleorubidus* | KCTC 1743$^T$ |
| 24 | *S. collinus* | KCTC 9713$^T$ |
| 25 | *S. corchorusii* | KCTC 9715$^T$ |
| 26 | *S. diastaticus* | KCTC 9142$^T$ |
| 27 | *S. djakartensis* | KCTC 9722$^T$ |
| 28 | *S. erumpens* | KCTC 9729$^T$ |
| 29 | *S. fulvissimus* | KCTC 9779$^T$ |
| 30 | *S. galilaeus* | KCTC 1919$^T$ |
| 31 | *S. griseochromogenes* | KCTC 9027$^T$ |
| 32 | *S. griseolus* | KCTC 9028$^T$ |
| 33 | *S. griseoviridis* | KCTC 9780$^T$ |
| 34 | *S. humiferus* | KCTC 9116$^T$ |
| 35 | *S. hygroscopicus* | KCTC 9782$^T$ |
| 36 | *S. minutiscleroticus* | KCTC 9123$^T$ |
| 37 | *S. murinus* | KCTC 9492$^T$ |
| 38 | *S. nodosus* | KCTC 9035$^T$ |
| Non-reference Strains *Streptomyces* | | |
| 1 | *S. hygroscopicus* | KCTC 9030 |
| 2 | *S. hygroscopicus* | KCTC 9031 |
| 3 | *S. hygroscopicus* | KCTC 9069 |
| 4 | *S. albus* | KCTC 1136 |
| 5 | *S. albus* | KCTC 1533 |
| Other Actinomycetes | | |
| 1 | *R. equi* | KCTC 9082 |
| 2 | *T. paurometabola* | KCTC 9821 |

Abbreviation:
KCTC: Korean Collection for Type Cultures

REFERENCE EXAMPLE 2

Total 15 strains of 7 *S. scabiei* strains, 1 *S. acidiscabies* strain and 4 *S. turgidiscabies* strains known as potato scab pathogenic microorganisms, and 1 *S. bottropensis* strain, 1 *S. disastatochromogenes* strain and 1 *S. neyagawaensis* strain showing a close relationship to the potato scab pathogenic microorganism in a phylogenetic taxonomy were subjected to sequencing analysis of groEL2 gene, and total 20 isolated strains obtained from Kangwon-do and Jeju-do derived potato scab pathogenic tissues were subjected to comparison analysis of the nucleotide sequences of groEL2 gene (Table 2).

TABLE 2

| No | Name | Source | No | Name | Source |
|---|---|---|---|---|---|
| Potato scab causing reference strains | | | | | |
| 1 | S. scabiei | ATCC 40173[T] | 2 | S. scabiei | DSMZ 40961 |
| 3 | S. scabiei | DSMZ 40962 | 4 | S. scabiei | IFO 3111 |
| 5 | S. scabiei | IFO 13767 | 6 | S. scabiei | IFO 13768 |
| 7 | S. scabiei | IFO 12914 | 8 | S. acidiscabies | ATCC 49003[T] |
| 9 | S. turgidiscabies | ATCC 700248[T] | 10 | S. turgidiscabies | IFO 16079 |
| 11 | S. turgidiscabies | IFO 16080 | 12 | S. turgidiscabies | IFO 16081 |
| 13 | S. bottropenis | IFO 13023 | 14 | S. disastatochromogenes | IFO 13389 |
| 15 | S. neyagawaensis | IFO 3784 | | | |
| Isolated Potato scab causing strains | | | | | |
| Strains isolated from Kangwon-do | | | | | |
| 16 | Kangwon-S20 | Kangwon-do | 17 | Kangwon-S27 | Kangwon-do |
| 18 | Kangwon-S28 | Kangwon-do | 19 | Kangwon-S32 | Kangwon-do |
| 20 | Kangwon-S33 | Kangwon-do | 21 | Kangwon-S34 | Kangwon-do |
| 22 | Kangwon-S48 | Kangwon-do | 23 | Kangwon-S51 | Kangwon-do |
| 24 | Kangwon-S53 | Kangwon-do | 25 | Kangwon-S56 | Kangwon-do |
| 26 | Kangwon-S58 | Kangwon-do | 27 | Kangwon-S59 | Kangwon-do |
| 28 | Kangwon-S71 | Kangwon-do | | | |
| Strains isolated from Jeju-do | | | | | |
| 29 | Jeju-H11 | Jeju-do | 30 | Jeju-H12 | Jeju-do |
| 31 | Jeju-H16 | Jeju-do | 32 | Jeju-H17 | Jeju-do |
| 33 | Jeju-H18 | Jeju-do | 34 | Jeju-H19 | Jeju-do |
| 35 | Jeju-H20 | Jeju-do | | | |

EXAMPLE 1

Preparation of groEL2 Primer Specific for *Streptomyces* Species

Specific forward (STGROF1) and reverse primers (STGROR2) were designed to be capable of amplifying groEL2 gene fragment in all *Streptomyces* species. *S. lividans* (GenBank No. X95971) and *S. albus* (GenBank No. M76658), whose full-length nucleotide sequences of groEL2 gene were already sequenced for other purposes, and *T. paurometabola* (GenBank No. AF352578), which belongs to *Tsukamurella* species closely related to *Streptomyces* species in a phylogenetic tree, were subjected to sequencing analysis, and forward primer STGROF1 (5'-CCATCGCCAAG-GAGATCGAGCT-3': SEQ ID NO: 1) and reverse primer STGROR2 (5'-TGAAGGTGCCRCGGATCTTGTT-3': SEQ ID NO: 2) that are capable of specifically amplifying all *Streptomyces* species were prepared therefrom (FIG. 1). The primer pair of STGROF1 and STGROR2 is new which has not been used previously for amplifying *Streptomyces* species.

FIG. 1 shows the recognition sites of primers employed in the present invention. The inventive primer pair of STGROF1 and STGROR2 was designed to target a total 648-bp of groEL2 gene fragment corresponding to the nucleotide sequence ranging from 161 to 808 in 1623-bp of the full-length groEL2 gene of *S. albus*. A forward primer consisting of 22 nucleotides corresponding to the base sequence ranging from 161 to 182 and a reverse primer consisting of 22 nucleotides corresponding to the base sequence ranging from 787 to 808 in the nucleotide sequence of *S. albus* were employed to amplify 648-bp of the groEL2 gene fragment of *Streptomyces* species. The recognition sites of the primers are phylogenetically conserved regions that show a 100% sequence homology to not only *S. lividans* and *S. albus* belong to *Streptomyces* species but also *T. paurometabola* belong to a different group from *Streptomyces* species.

EXAMPLE 2

Preparation of 420-bp groEL2 Fragment of *Streptomyces* Species

1) DNA Extraction

DNA was extracted according to a BB/P (Bead beater phenol) method. Cultured cells were harvested and suspended in a TEN buffer solution (Tris-HCl 10 mM, EDTA 1 mM, NaCl 100 mM: pH 8.0). The suspension was re-suspended in the mixture of 100 µl (packing volume) ultrafine magnetobead solution (diameter 0.1 mm; Biospec Products, Bartlesville, Okla., U.S.A.) and 100 µl phenol/chloroform/ isopropylalcohol (50/49/1) solution and subjected to shaking for 1 min with a mini beater to disrupt cells. After centrifuging the resulting solution at 12,000 rpm for 5 min, the supernatant (100 µl) was transferred to a new tube and added with 60 µl isopropylalcohol. The tube was then centrifuged at 15,000 rpm for 15 min to produce a pellet. The pellet was washed with 70% ethanol, and then, DNA was recovered in 60 µl TE buffer solution (pH 8.0, 10 mM Tris-HCl, 1 mM EDTA).

2) PCR Amplification of groEL2 Gene

Forward primer STGROF1 and reverse primer STGROR2 specific for *Streptomyces* species were employed. The PCR reaction solution was prepared by mixing 50 ng of template DNA, 20 pmole each of SRPOF1 and SRPOR2 primers, and AccuPower PCR PreMix (Bioneer, Korea) consisting of 2 units of Taq polymerase, 10 mM dNTP, 10 mM Tris-HCl (pH 8.3) and 1.5 mM MgCl$_2$, adjusted to a final volume of 20 μl. The PCR condition consisted of 30 cycles of: 1 min at 95° C. (denaturation), 45 sec at 62° C. (annealing) and 90 sec at 72° C. (extension) after the initial denaturation for 5 min at 95° C., and 5 min at 72° C. (final amplification) (Model 9600 thermocycler, Perkin-Elmer cetus). After PCR was completed, the reaction mixtures were subjected to 1% agarose gel electrophoresis to examine whether 648-bp of PCR product was amplified.

Figure 2:
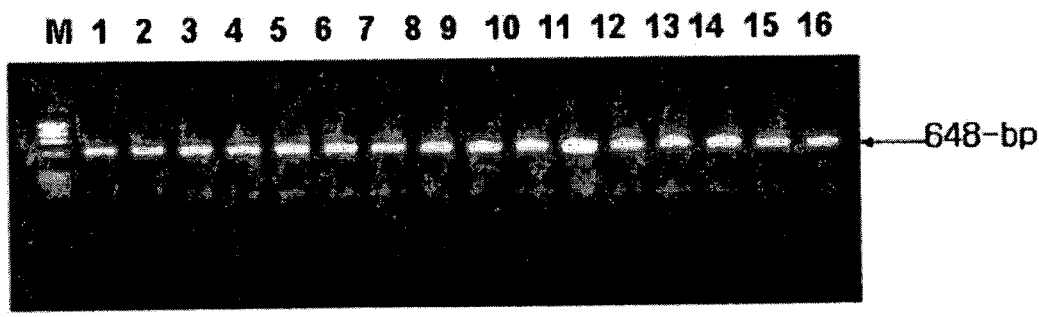
FIG. 2 shows the result of electrophoresis of 648-bp groEL2 gene fragment amplified from a reference strain of *Streptomyces* species using a primer pair specific for *Streptomyces* species.

As a result of PCR using the primer pair specific for *Streptomyces* species selected above, it was found that 648-bp of groEL2 gene fragments were amplified from all 40 reference strains (FIG. 2). Further, it was found that the inventive primer pair could amplify *Rhodococcus* and *Tsukamurella* species belong to rare actinomycete species as well as *Streptomyces* species.

Figure 3:
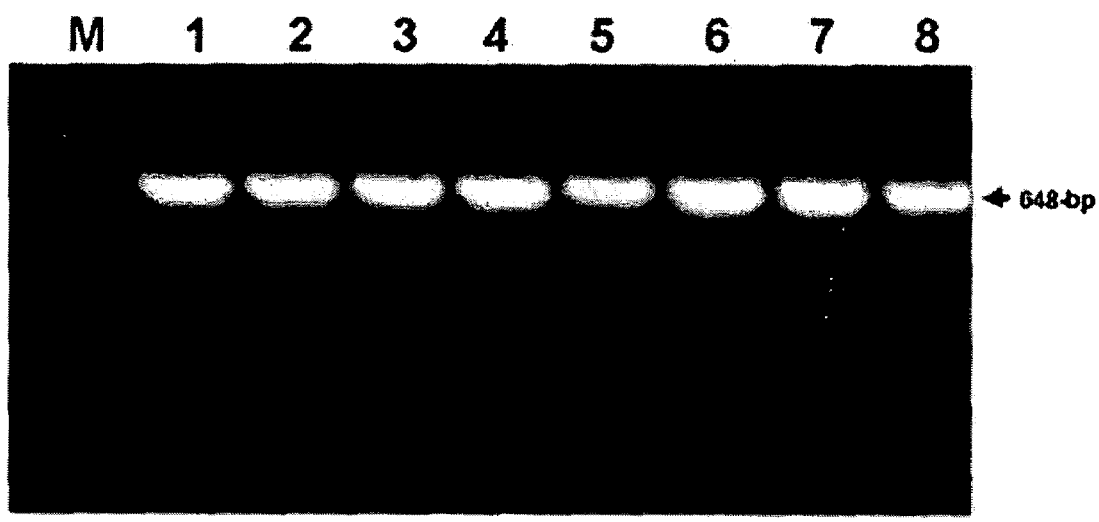
FIG. 3 shows the result of electrophoresis of 648-bp groEL2 gene fragment amplified from a reference strain of a potato scab pathogenic microorganism using a primer pair specific for *Streptomyces* species.

Meanwhile, it was found that the inventive primer pair is capable of amplifying 648-bp of groEL2 gene fragments from 15 potato scab pathogenic reference strains and 20 isolated strains (FIG. 3).

3) Purification of PCR Products

After 1% agarose gel electrophoresis was completed, gel slices corresponding to 648-bp PCR products of *Streptomyces* reference strains were excised, transferred to a new tube, and subjected to DNA extraction. DNA extraction and purification were carried out using a Qiaex system (Qiagen, Germany). The tube was added with gel dissolving solution QX1 (500 μl) and then incubated at 50° C. for 15 min to completely dissolve the gel. Then, 10 μl of gel bead solution was added thereto and the mixture was kept at 50° C. for 15 min. In the meantime, the tube was subjected to vortexing for 10 sec at intervals of 1 min to spread the bead equally. The reaction mixture was washed once with QX1, twice with QF and dried at 45° C. for 10 min, and then DNA was recovered in 20 μl of TE buffer solution.

EXAMPLE 3

Automatic Sequencing Analysis of groEL2 Fragment

Automatic sequencing analysis was carried out using the gel-eluting product as a target DNA. The reaction mixture was prepared by mixing 60 ng of template DNA, 1.2 pmole of primer and 2 μl of BigDye terminator cycle sequencing kit (PE Appied Biosystems), adjusted to a final volume of 10 μl. The reaction condition consisted of 25 cycles of: 10 sec at 95° C., 10 sec at 60° C. and 4 min at 60° C. (Model 9600 thermocycler, Perkin-Elmer cetus). After the reaction was completed, DNA was extracted according to an ethanol precipitation method. In particular, after 180 μl of distilled water and 10 μl of 3 M sodium acetate were added to the reaction mixture adjusted to a final volume of 200 μl, 2 volumes of 100% ethanol was added thereto, and the mixture was mixed well. The reaction mixture was subjected to centrifugation at 15,000 rpm for 20 min to precipitate DNA. Then, 500 μl of 70% ethanol was added thereto and the precipitated DNA was subjected to centrifugation at 15,000 rpm for 20 min for washing. DNA was recovered using Deionized Formimide (PE Applied Biosystems). Thus purified DNA was heated at 95° C. for 5 min to denature into a single strand DNA and subjected to electrophoresis using an ABI 3100 system for 2.5 hrs to analyze the nucleotide sequence.

The sequencing analysis was carried out in one direction using the forward primer STGROF1, and accordingly, the groEL2 gene fragment (420-bp or 423-bp) in the 648-bp of full-length nucleotide sequence was determined.

The PCR product was purified according to the method described above, and subjected to automatic sequencing analysis without going through a cloning process. A 420-bp of fragment corresponding to the nucleotide sequence ranging from 232 to 631 in the full-length groEL2 gene of *S. albus* was sequenced as shown in FIG. 1. As a result, the nucleotide sequences of all 420-bp fragments amplified from 40 reference strains and 35 potato scab causing strains were determined without a certain ambiguous result (if several copies of a target gene exist in a chromosome and their nucleotide sequences are different from each other, it is impossible to determine the exact nucleotide sequence since the nucleotide sequence at the other position maybe overlapped with that of the correct position in a direct sequencing analysis).

As a result of comparing the nucleotide sequences in multi-alignment, all 40-reference strains had a nucleotide sequence of their own which are different from each other. Namely, they showed interspecies variation. For a certain gene to be targeted in identifying a bacterial strain, it is a prerequisite that the interspecies variation be preserved among species. It was found that the inventive identification method met the requirement.

Further, except 3 strains (*S. ambofaciens, S. erumpens* and *S. murinus*) having 423-bp of fragment wherein 1 amino acid, i.e., 3-bp (GCG), was inserted at the 301$^{st}$ residue based on the full-length groEL2 nucleotide sequence of *S. albus*, all the nucleotide sequences of 37 reference strains encoded 420-bp of groEL2 gene fragment without insertion or deletion in the multi-alignment. Namely, there was no gap in the multi-alignment. 16S rDNA shows a gap at a high frequency in the alignment. It has been reported that the gap makes an error in building an entire phylogenetic tree since the gap is apt to be analyzed by removing all the aligned nucleotides corresponding to that region during the multi-alignment, it is likely. Accordingly, the result described above demonstrated the superiority of the inventive groEL2 gene for identifying a bacterial strain.

As a result of multi-alignment using a polypeptide encoded by 420-bp of groEL2 gene fragment which consists of 140 amino acids that corresponds to the region ranging from the 78$^{th}$ to the 217$^{th}$ residues in the amino acid sequence of full-length groEL2 protein of *S. albus*, it was found that all 37 reference strains encoded the polypeptide consisting of 140 amino acids except 3 strains of *S. ambofaciens, S. erumpens* and *S. murinus* having an insertion of alanine at the 101$^{st}$ residue in the amino acid sequence of full-length groEL2 protein of *S. albus* which encodes a polypeptide consisting of 141 amino acids. Further, it was found that 33 alleles existed in 40 reference strains based on the sequence homology of amino acid. These results suggested that the polypeptide encoded thereby as well as the nucleotide sequence of groEL2 gene were efficiently used for the identification of *Streptomyces* species different from 16S rDNA which does not encode any polypeptides.

Meanwhile, the results for identifying potato scab causing strains among *Streptomyces* species were as follows.

As a result of comparing the nucleotide sequences of 15 potato scab causing reference strains, it was found that three different species of *S. scabiei, S. acidiscabies* and *S. turgidiscabies* known as potato scab pathogenic microorganisms had their own nucleotide sequences different from each other and belonged to a group different from each other in the phylogenetic tree. It was also found that *S. scabiei* significantly represents various genotypes in the phylogenetic tree different from other two strains that showed closely related genotypes. These results coincided with the previous report that these species are composed of diverse genotypes. Namely, as a result of comparing the sequence homology of each 420-bp groEL2 nucleotide sequence of 7 reference strains belong to *S. scabiei*, they showed a sequence homology ranging from 88.9 to 100%. *S. scabiei* was divided into 4 groups based on the phylogenetic tree made by using the sequence homology. Group I included two reference strains of ATCC 49173T and DSMZ 40962 that showed a 100% sequence homology; Group II, two reference strains of IFO 12914 and IFO 3111 that show a 98.1% sequence homology; Group III, two reference strains of IFO 13767 and IFO 13768 that show a 100% sequence homology; and Group IV, one reference strain of DSMZ 40961. It was found that while 7 reference strains of *S. scabiei* showed interspecies variation, 4 reference strains (ATCC 700248T, IFO 16079, IFO 16080 and IFO 16081), which belong to *S. turgidiscabies*, showed a 100% sequence homology with each other.

EXAMPLE 4

Arrangement and Homology Analysis of groEL2 Nucleotide Sequence and Preparation of Phylogenetic Tree The nucleotide sequences (420-bp or 423-bp) of groEL2 gene fragments of 40 *Streptomyces* reference strains analyzed by an automatic sequencing method were subjected to multi-alignment using a Megalign program of DNAstar software to build a groEL2 database. Once 420-bp of the nucleotide sequences were translated into a polypeptide consisting of 140 amino acids in the Megalign program, the translated amino acids were subjected to multi-alignment according to a Clustal method stored in the Megalign program. Then, 140 amino acids thus aligned were converted into 420 nucleotides to build a database for identifying actinomycete species. Sequence homology to each nucleotide sequence of 40 strains was analyzed by applying the aligned database to a sequence distance method stored in the Megalign program.

After the multi-alignment of nucleotide sequence, sequence homology of 40 reference strains were examined according to the method described above. As a result, all the reference strains showed a different in sequence homology with each other. As a result of analyzing the sequence homology of 38 *Streptomyces* species, they showed a sequence homology ranging from 88.4% (between *S. griseolus* and *S. albus*) to 99.1% (between *S. humiferus* and *S. ambofaciens*).

Accordingly, it was found that there was sequence heterogeneity ranging from 0.9% to 11.6% among *Streptomyces* species. From these results, it was confirmed that the inventive groEL2 gene has a higher interspecies variation thus being regarded as the most important feature of a target gene for identifying a bacterial strain than 16S rDNA which showed 3% and less of sequence heterogeneity between *Streptomyces* species. When the nucleotide sequences of 38 *Streptomyces* reference strains were compared with those of *R. equi* and *T. paurometabola*, they showed 85.5% (between *S. anandii* and *R. equi*) and less of a sequence homology.

As a result of examining the sequence homology of polypeptides encoded by above 420-bp groEL2 fragments of 38 *Streptomyces* species, they showed a sequence homology ranging from 91.4% (between *S. griseolus* and *S. albus*) to 100%. When the amino acid sequences of polypeptides derived from 38 *Streptomyces* species were compared with those of *R. equi* and *T. paurometabola*, they showed 87.9% (between *S. anandii* and *R. equi*) or less of a sequence homology.

A phylogenetic relationship between each species was analyzed from a phylogenetic tree, which was built by using the MEGA software. The aligned 420-bp nucleotide sequences of 40 strains were analyzed by a Neighbor-Joining method based on a Juke-Cantor distance measuring method and a pair wise detection method to build a phylogenetic tree. Bootstrap analysis was carried out by 100 replications.

The sequence homology and phylogenetic tree of polypeptides encoded by groEL2 gene fragments were analyzed by translating 420-bp of the nucleotide sequences into 140 amino acids using the Megalign program and multi-aligning the amino acid sequences according to the Clustal method stored in the Megalign program.

Figure 4:
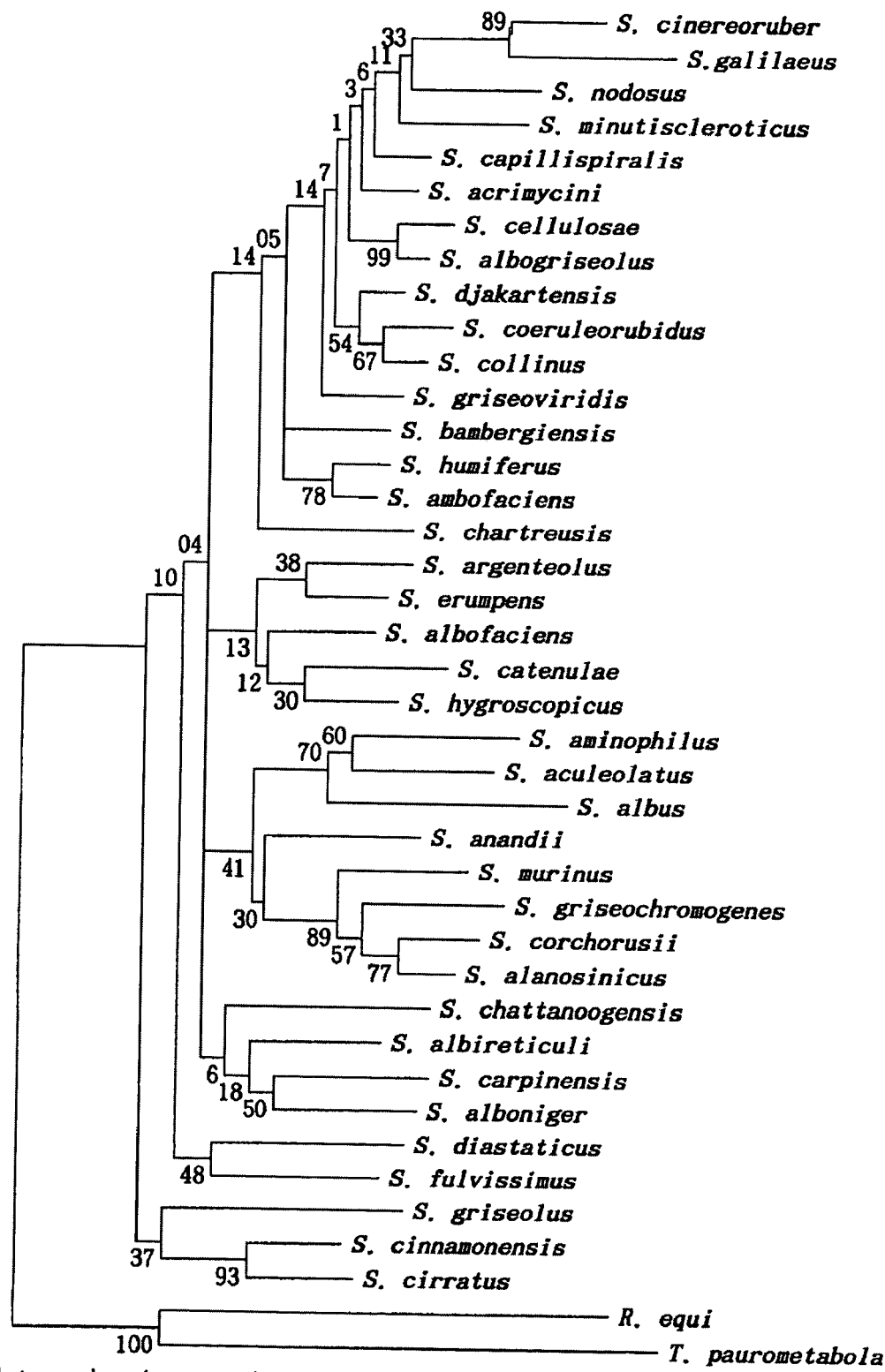
FIG. 4 shows the phylogenetic tree of 40 reference strains of *Streptomyces* species formed by using the nucleotide sequences of 420-bp groEL2 gene fragments.

The aligned nucleotide sequences of 40 strains were subjected to build a Neighbor-Joining phylogenetic tree using the Mega software described above. As a result, it was found that all the 40 strains had a nucleotide sequence of their own which are different from each other and 40 kinds of characteristic fragments. Further, it was found that 38 strains of *Streptomyces* species formed an individual group as against *R. equi* and *T. paurometabola* (FIG. 4).

Figure 5:
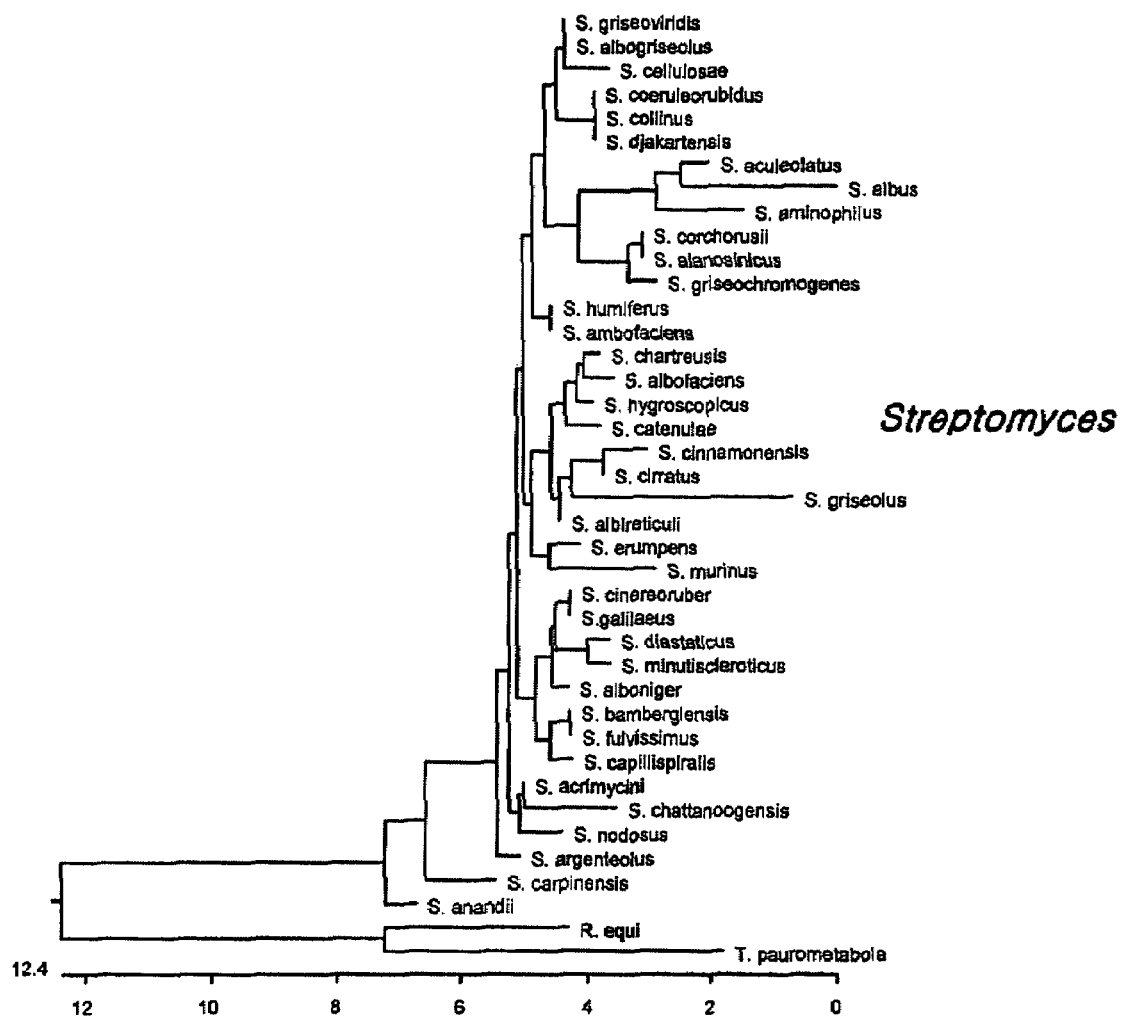
FIG. 5 shows the phylogenetic tree of 40 reference strains of *Streptomyces* species formed by using the polypeptide sequences consisting of 140 amino acids encoded by 420-bp groEL2 gene fragments.

As a result of multi-aligning the polypeptides according to the Clustal method in the Megalign program, it was found that 33 alleles coding different polypeptides from each other among 40 reference strains formed the same number of fragment. Similarly, 33 fragments formed an individual group as against *R. equi* and *T. paurometabola* (FIG. 5).

EXAMPLE 5

Identification of Non-reference Strains by Comparative Nucleotide Sequence Analysis Using a Reference Strain Database As shown in Table 1, total 5 non-reference strains of 3 *S. hygroscopicus* (KCTC 9030, KCTC 9031 and KCTC 9069) and 2 *S. albus* (KCTC 1136 and KCTC 1533) were subjected to identification. The non-reference strains were identified by the following steps of: analyzing the nucleotide sequences of 420-bp groEL2 fragments of each strain according to the method described above; inputting the analyzed nucleotide sequences into the Megalign program of DNAstar software; conducting multi-alignment described above; and preparing a phylogenetic tree according to the Neighbor-Joining method of Mega software.

To examine whether the reference strain database (55 strains consisting of 40 reference strains of *Streptomyces* species and 15 reference strains of potato scab pathogenic microorganisms) can be applied to the identification of a bacterial strain in practice, total 5 non-reference strains of 3 *S. hygroscopicus* (KCTC 9030, KCTC 9031 and KCTC 9069) and 2 *S. albus* (KCTC 1136 and KCTC 1533); and total 20 potato scab pathogenic microorganisms of 13 strains isolated from Kangwon-do and 7 strains isolated from Jeju-do described in Table 2 were subjected to comparative analysis of the nucleotide sequence of groEL2 gene.

Figure 6:
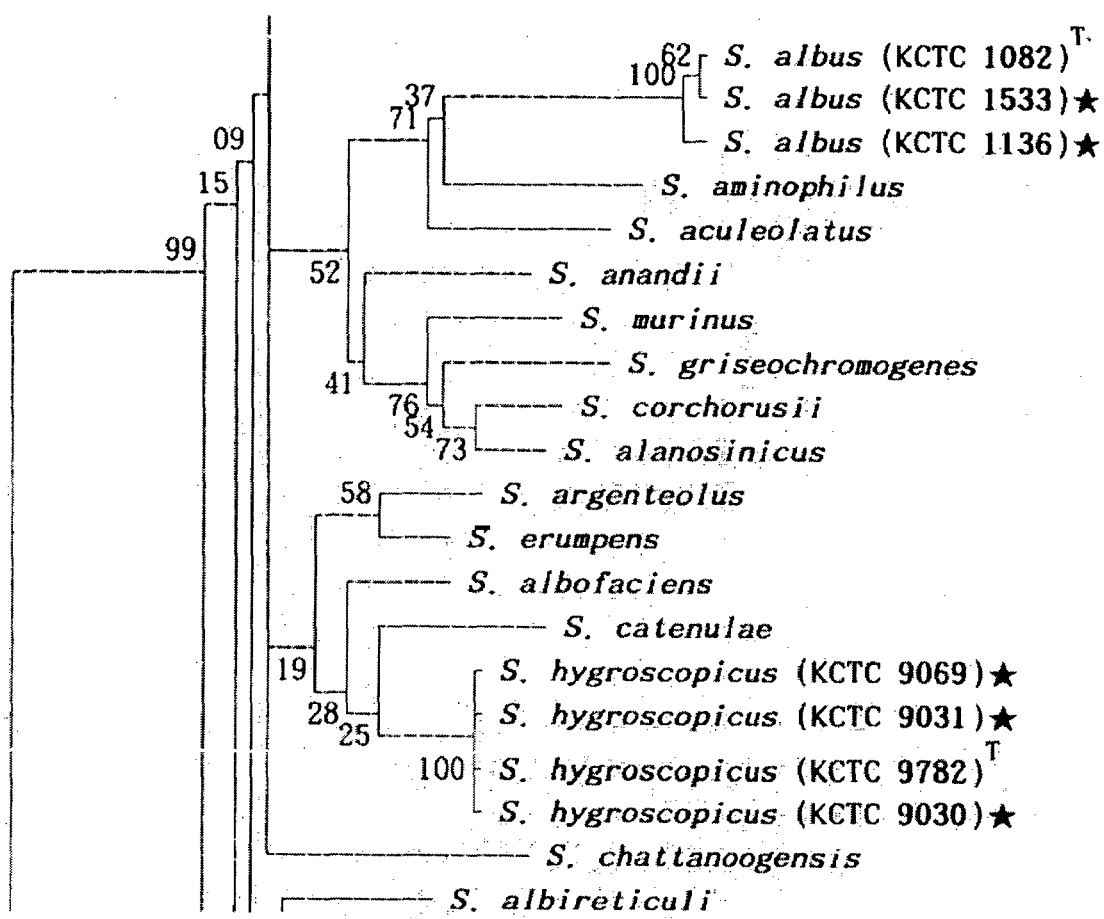
FIG. 6 shows the result of identifying 5 non-reference strains by comparing the nucleotide sequences of 420-bp groEL2 fragments.

As a result, 3 strains of *S. hygroscopicus* (KCTC 9030, KCTC 9031 and KCTC 9069) showed a sequence homology of 100%, 99.8% and 99.8%, respectively, and were located at a position corresponding to *S. hygroscopicus* (KCTC 9782; reference strain) in the phylogenetic tree (FIG. 6). Further, 2 strains of *S. albus* (KCTC 1136 and KCTC 1533) showed a sequence homology of 99.8% and 100%, respectively, and were located at a position corresponding to *S. albus* (KCTC 1082; reference strain) (FIG. 6).

Figure 7:
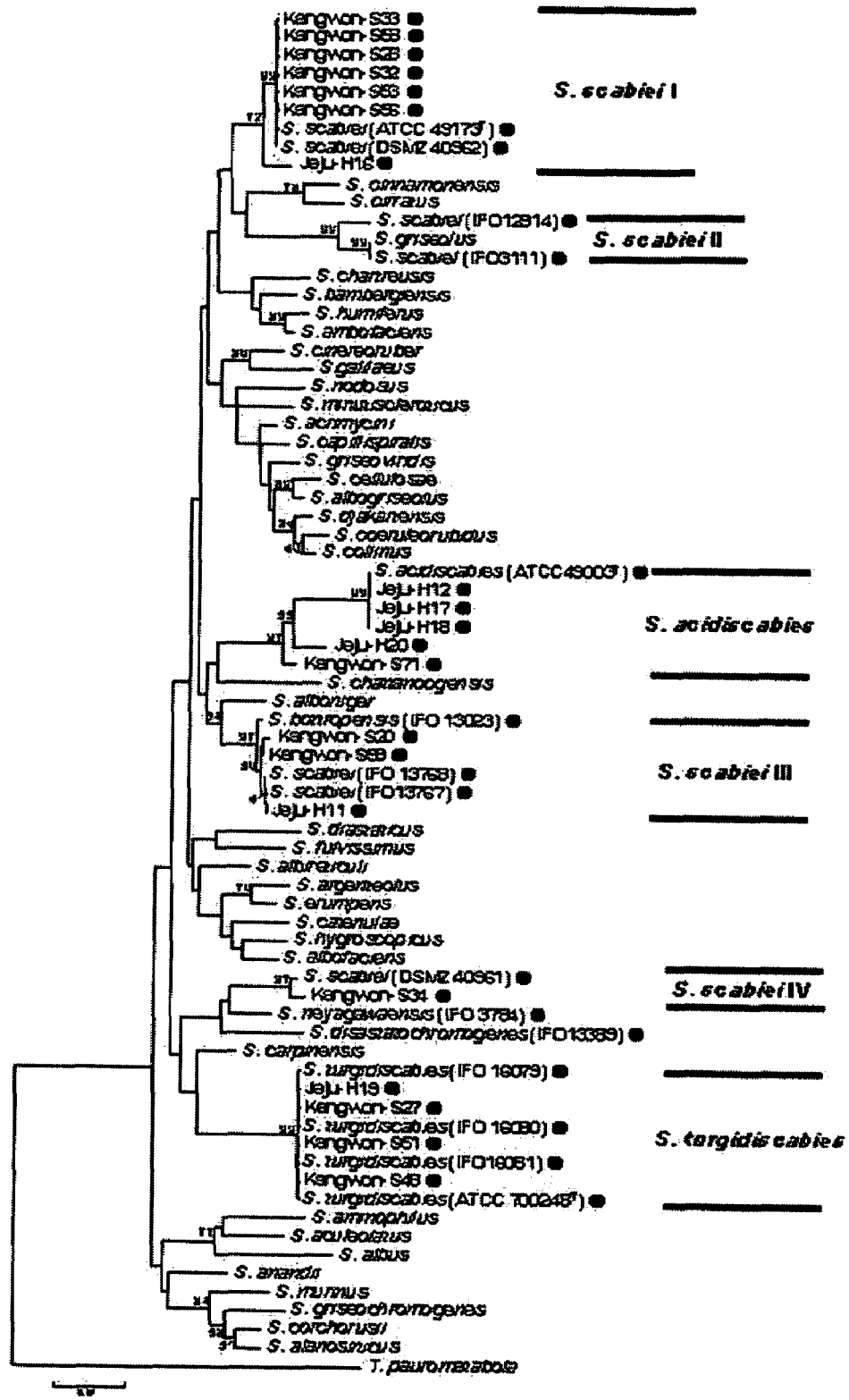
FIG. 7 shows the phylogenetic tree of 40 reference strains of *Streptomyces* species, 15 reference strains of potato scab pathogenic microorganisms and 20 isolated strains formed by using the nucleotide sequences of 420-bp groEL2 fragments.

In addition, it was found that all 20 isolated strains belonged to a potato scab pathogenic group consisting of *S. scabiei, S. acidiscabies* and *S. turgidiscabies*. 11 isolated strains (9 strains isolated from Kangwon-do [Kangwon-S20, Kangwon-S28, Kangwon-S32, Kangwon-S33, Kangwon-S34, Kangwon-S53, Kangwon-S56, Kangwon-S58 and Kangwon-S59] and 2 Jeju-do isolated strains [Jeju-H11 and Jeju-H16]) out of total 20 strains (55%) belonged to *S. scabiei*. Coinciding with the previous report, *S. scabiei* was identified at the highest frequency in the present invention. It was confirmed that these species belong to three groups (Group I, III and IV) among four groups of *S. scabiei*. 7 strains of Kangwon-S28, Kangwon-S32, Kangwon-S33, Kangwon-S53, Kangwon-S56, Kangwon-S58 and Jeju-H16 showed a sequence homology ranging from 98.8% to 100% at higher frequency and belonged to Group I. 3 strains (Kangwon-S20, Kangwon-S59 and Jeju-H11) out of them showed a sequence homology ranging from 99.5% to 100% and belonged to Group II. Kangwon-S34 strain showed a sequence homology of 99.3% with the reference strain DSM 40961 and belonged to Group IV (FIG. 7).

5 strains [1 strain isolated from Kangwon-do (Kangwon-S71), 4 Jeju-do strains isolated (Jeju-H12, Jeju-H17, Jeju-H18 and Jeju-H20)] out of 20 strains showed a sequence homology ranging from 96.9% to 100% at 25% of isolation frequency and were identified as *S. scabiei*. Further, 4 strains [3 strains isolated from Kangwon-do (Kangwon-S27, Kangwon-S48 and Kangwon-S51), 1 strain isolated from Jeju-do (Jeju-H19)] showed a sequence homology of 100% with each other at 20% of isolation frequency and were identified as *S. turgidiscabies*.

While the embodiments of the subject invention have been described and illustrated, it is obvious that various changes and modifications can be made therein without departing from the spirit of the present invention which should be limited only by the scope of the appended claims.

What is claimed is:

1. A primer, which amplifies groEL2 gene fragment of at least one *Streptomyces* species, consisting of the nucleotide sequence of SEQ ID NO: 1.

2. A primer, which amplifies groEL2 gene fragment of at least one *Streptomyces* species, consisting of the nucleotide sequence of SEQ ID NO: 2.

3. An isolated groEL2 gene fragment from *Streptomyces* species consisting of a polynucleotide selected from the group consisting of the nucleotide sequences of SEQ ID NOs: 3 to 42.

4. An isolated groEL2 gene fragment from *S. scabiei* comprising SEQ ID NO: 43.

5. A method for identifying *Streptomyces* species comprising:
   a) amplifying groEL2 gene fragment of target microorganism using the primer according to claims 1 or 2;
   b) analyzing the nucleotide sequence of the groEL2 gene fragment thus amplified; and
   c) comparing the nucleotide sequence obtained in b) with that of groEL2 gene fragment of a reference strain.

6. The method of claim 5, wherein the microorganism is selected from the group consisting of *R. equi, S. acrimycini, S. aculeolatus, S. alanosinicus, S. albireticuli, S. albofaciens, S. albogriseolus, S. alboniger, S. albus, S. ambofaciens, S. aminophilus, S. anandii, S. argenteolus, S. bambergiensis, S. capillispiralis, S. carpinesis, S. catenulae, S. cellulosae, S. chartreusis, S. chattanoogensis, S. cinereoruber, S. cinnamonensis, S. cirratus, S. coeruleorubidus, S. collinus, S. corchorusii, S. diastaticus, S. djakartensis, S. erumpens, S. fulvissimus, S. galilaeus, S. griseochromogenes, S. griseolus, S. griseoviridis, S. humiferus, S. hygroscopicus, S. minutiscleroticus, S. murinus, S. nodosus, T. paurometabola, S. acidiscabies, S. bottropenis, S. disastatochromogenes, S. neyagawaensis, S. scabiei,* and *S. turgidiscabies*.

7. The method of claim 5, wherein the groEL2 gene fragment of a reference strain is selected from the group consisting of the nucleotide sequences of SEQ ID NOs: 3 to 42.

8. The method of claim 5, wherein the groEL2 gene fragment of a reference strain is selected from the group consisting of the nucleotide sequences of SEQ ID NOS 43-44, 47, 49-51, 55-61.

9. The method of claim 5, wherein c) further comprises multi-aligning the nucleotide sequences and forming a phylogenetic tree.

10. The groEL2 gene fragment of claim 4, wherein the fragment is SEQ ID NO: 43.

11. An isolated groEL2 gene fragment from a potato scab pathogenic microorganism consisting of a polynucleotide selected from the group consisting of the nucleotide sequences of any one of SEQ ID NOs: 44, 47, 49-51, 55-61.

12. An isolated groEL2 gene fragment produced by amplification from a microorganism using
   a) a primer consisting of the nucleotide sequence of SEQ ID NO: 1 and
   b) a primer consisting of the nucleotide sequence of SEQ ID NO: 2,
   wherein said microorganism is selected from the group consisting of *R. equi, S. acrimycini, S. aculeolatus, S. alanosinicus, S. albireticuli, S. albofaciens, S. albogriseolus, S. alboniger, S. albus, S. ambofaciens, S. aminophilus, S. anandii, S. argenteolus, S. bambergiensis, S. capillispiralis, S. carpinesis, S. catenulae, S. cellulosae, S. chartreusis, S. chattanoogensis, S. cinereoruber, S. cinnamonensis, S. cirratus, S. coeruleorubidus, S. collinus, S. corchorusii, S. diastaticus, S. djakartensis, S. erumpens, S. fulvissimus, S. galilaeus, S. griseochromogenes, S. griseolus, S. griseoviridis, S. humiferus, S. hygroscopicus, S. minutiscieroticus, S. murinus, S. nodosus, T. paurometabola, S. acidiscabies, S. bottropenis, S. disastatochromogenes, S. neyagawaensis, S. scabiei,* and *S. turgidiscabies*.

* * * * *

UNITED STATES PATENT AND TRADEMARK OFFICE
CERTIFICATE OF CORRECTION

PATENT NO. : 7,413,858 B2
APPLICATION NO. : 10/824527
DATED : August 19, 2008
INVENTOR(S) : Bum-Joon Kim et al.

It is certified that error appears in the above-identified patent and that said Letters Patent is hereby corrected as shown below:

Claim 12, col. 50, line 49, "S. minutiscieroticus" should read -- S. minutiscleroticus --.

Signed and Sealed this

Twenty-eighth Day of October, 2008

JON W. DUDAS
*Director of the United States Patent and Trademark Office*

SEQUENCE LISTING

```
<160> NUMBER OF SEQ ID NOS: 61

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccatcgccaa ggagatcgag ct                                               22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tgaaggtgcc rcggatcttg tt                                               22

<210> SEQ ID NO 3
<211> LENGTH: 420
<212> TYPE: DNA
<213> ORGANISM: Streptomyces acrimycini

<400> SEQUENCE: 3
aagaagacgg acgacgtcgc cggtgacggt acgaccaccg cgaccgttct cgcccaggcc      60
ctggtcaggg agggcctgcg caacgtcgcc gccggcgcca acccgatggc tctgaagcgc     120
ggcatcgaga aggccgtcga ggccgtctcc gccgccctgc tggagcaggc gaaggacgtc     180
gagaccaagg agcagatcgc ctccacggcc tccatctccg ccgccgacac ccagatcggc     240
gagctcatcg ccgaggccat ggacaaggtc ggcaaggaag gcgtcatcac cgtcgaggag     300
tcccagacct tcggtctgga gctggagctc accgagggta tgcgcttcga caagggctac     360
atctcggcgt acttcgccac cgacatggag cgtatggagg ccgtcctcga cgacccgtac     420

<210> SEQ ID NO 4
<211> LENGTH: 420
<212> TYPE: DNA
<213> ORGANISM: Streptomyces aculeolatus
```

-continued

<400> SEQUENCE: 4

| | | |
|---|---|---|
| aagaagacgg acgacgtcgc cggtgacggc acgaccaccg cgaccgtcct cgcccaggcc | 60 |
| ctggtcaagg agggcctgcg gaacgtggcc gccggcgcca acccgatggc gctgaagcgc | 120 |
| ggcatcgaga aggccaccga ggccgtctcc gccgccctgc tggagcaggc caaggacgtg | 180 |
| gagaccaagg agcagatcgc ctccaccgcc tccatctccg ccggcgacac ccagatcggc | 240 |
| gagctgatcg ccgaggccat ggacaaggtc ggcaaggaag gcgtcatcac cgtcgaggag | 300 |
| tcgcagacct tcgggctgga gcttgagctc accgagggca tgcgcttcga caagggctac | 360 |
| atctccgcct acttcgccac cgacatggag cgcatggagg cggagctcga ggacccgtac | 420 |

<210> SEQ ID NO 5
<211> LENGTH: 420
<212> TYPE: DNA
<213> ORGANISM: Streptomyces alanosinicus

<400> SEQUENCE: 5

| | | |
|---|---|---|
| aagaagacgg acgacgtcgc cggtgacggt acgaccaccg cgaccgtgct cgcccaggcc | 60 |
| ctggtcaagg aaggcctgcg caacgtcgcc gccggcgcca acccgatggc cctgaagcgc | 120 |
| ggtatcgaga aggccgtcga ggccgtctcc gccgccctgc tggagcaggc gaaggacgtc | 180 |
| gagaccaagg agcagatcgc ctccaccgcg tccatctccg ccgccgacac ccagatcggc | 240 |
| gagctcatcg ccgaggccat ggacaaggtc ggcaaggaag gcgtcatcac cgtcgaggag | 300 |
| agcaacacct tcggtctgga gcttgagctc accgagggca tgcgcttcga caagggctac | 360 |
| atctccgcct acttcgcgac cgacatggag cgcatggagg cggtgctcga ggacccgtac | 420 |

<210> SEQ ID NO 6
<211> LENGTH: 420
<212> TYPE: DNA
<213> ORGANISM: Streptomyces albireticuli

<400> SEQUENCE: 6

| | | |
|---|---|---|
| aagaagacgg acgacgtcgc cggtgacggc acgacgaccg cgaccgtcct cgcccaggcg | 60 |
| ctggtccgcg agggtctgcg caacgtggcc gccggtgcca acccgatggc cctgaagcgt | 120 |
| ggcatcgaga aggccgtcga ggccgtctcc gccgccctgc tcgagcaggc caaggacgtg | 180 |
| gagaccaagg agcagatcgc ctccaccgcc tccatctccg ccgccgacac ccagatcggc | 240 |
| gagctcatcg ccgaggcgat ggacaaggtc ggcaaggaag gcgtcatcac cgtcgaggag | 300 |
| tcccagacct tcggtctgga gctggagctc accgagggta tgcgcttcga caagggctac | 360 |
| atctcggcgt acttcgccac cgacatggag cgtatggagg cgtcgctcga cgacccgtac | 420 |

<210> SEQ ID NO 7
<211> LENGTH: 423
<212> TYPE: DNA
<213> ORGANISM: Streptomyces albofaciens

<400> SEQUENCE: 7

| | | |
|---|---|---|
| aagaagacgg acgacgtcgc cggtgacggc acgaccaccg cgaccgtcct ggcccaggcc | 60 |
| ctggtcacag cggagggcct gcgcaacgtc gccgccggcg ccaacccgat ggccctcaag | 120 |
| cgcggtatcg agcgcgccgt cgaggccgtc tccgccgccc tgctggagca ggcgaaggac | 180 |
| gtggagacca aggagcagat cgcctccacc gcctccatct ccgccgccga cacccagatc | 240 |
| ggcgagctga tcgccgaggc catggacaag gtcggcaagg aaggcgtcat caccgtcgag | 300 |

```
gagtcccaga ccttcggtct ggaactggag ctcaccgagg gtatgcgctt cgacaagggc    360
tacatctcgg cgtacttcgc caccgacatg gagcgtatgg aggcgtcgct cgacgacccg    420
tac                                                                  423

<210> SEQ ID NO 8
<211> LENGTH: 420
<212> TYPE: DNA
<213> ORGANISM: Streptomyces albogriseolus

<400> SEQUENCE: 8
aagaagacgg acgacgtcgc cggtgacggt acgaccacgg cgaccgttct cgcccaggcc     60
ctggtcaagg agggcctgcg caacgtcgcc gccggcgcca acccgatggc cctgaagcgc    120
ggtatcgaga aggccgtcga ggccgtctcc gccgcctcc tggagcaggc gaaggacgtg    180
gagaccaagg agcagatcgc ctccacggcc tccatctccg ccgccgacac ccagatcggc    240
gagctcatcg ccgaggccat ggacaaggtc ggcaaggaag cgtcatcac cgtcgaggag    300 tcccagacct tcggtctgga gctggagctc accgagggta tgcgcttcga caagggctac    360
atctcggcgt acttcgccac cgacatggag cgtatggagg ccgtcctcga cgacccgtac    420

<210> SEQ ID NO 9
<211> LENGTH: 420
<212> TYPE: DNA
<213> ORGANISM: Streptomyces alboniger

<400> SEQUENCE: 9
aagaagacgg acgacgtcgc cggtgacggc acgacgaccg cgaccgtcct ggcccaggcc     60
ctggtgcgcg agggtctgcg caacgtggcc gccggtgcca acccgatggc cctcaagcgc    120
ggcatcgaga aggccgtcga ggccgtctcc ggtgccctcc tcgagcaggc gaaggatgtc    180
gagaccaagg agcagatcgc ttccacggcc tccatctccg ccgccgacac ccagatcggc    240
gagctgatcg ccgaggccat ggacaaggtc ggcaaggaag cgtcatcac cgtcgaggag    300 tcccagacct tcggtctgga gctggagctc accgagggta tgcgcttcga caagggctac    360
atctcggcgt acttcgccac cgacatggag cgtatggagg cgtcgctcga cgacccgtac    420

<210> SEQ ID NO 10
<211> LENGTH: 420
<212> TYPE: DNA
<213> ORGANISM: Streptomyces albus

<400> SEQUENCE: 10
aagaagacgg acgacgtcgc cggtgacggc acgacgaccg cgaccgtcct ggcccaggcg     60
ctggtccgcg agggtctgcg caacgtcgcc gcgggcgcca acccgatggc cctcaagcgc    120
ggtatcgagc aggccaccga ggctgtctcc gctgccctgc tggagcaggc caaggacatc    180
gagaccaagg agcagatcgc ctccaccgcc tcgatctccg ccggcgacat ccagatcggt    240
gagctgatcg ccgaggccat ggacaaggtc ggcaaggaag cgtcatcac cgtcgaggag    300 tcgcagacct tcggtctcga gctggagctc accgagggca tgcgcttcga caagggctac    360
atctccgcct acttcgccac cgacatggag cgcatggagg cggagctcga ggacccgtac    420

<210> SEQ ID NO 11
<211> LENGTH: 420
<212> TYPE: DNA
<213> ORGANISM: Streptomyces ambofaciens

<400> SEQUENCE: 11
```

```
aagaagacgg acgacgtcgc cggtgacggt acgaccaccg cgaccgttct cgcccaggcc    60
ctggtcaagg aaggcctgcg caacgtcgcg gccggcgcca acccgatggc cctgaagcgc   120
ggcatcgaga aggccgtcga ggccgtctcc gccgccctgc tggagcaggc gaaggacgtc   180
gagaccaagg agcagatcgc ctccacggcc tccatctccg ccgccgacac ccagatcggc   240
gagctcatcg ccgaggccat ggacaaggtc ggcaaggaag gcgtcatcac cgtcgaggag   300
tcccagacct tcggtctgga gctggagctc accgagggta tgcgcttcga caagggctac   360
atctcggcgt acttcgccac cgacatggag cgtatggagg cgtcgctcga cgacccgtac   420

<210> SEQ ID NO 12
<211> LENGTH: 420
<212> TYPE: DNA
<213> ORGANISM: Streptomyces aminophilus

<400> SEQUENCE: 12
aagaagacgg acgacgtcgc ctgtgacggc acgacgaccg cgaccgtcct ggcccaggcc    60
ctggtcaagg agggcctgcg caacgtcgcg gccggcgcca acccgatggc cctgaagcgc   120
ggcatcgagc gcgccaccga ggccgtctcc gccgccctgc tggagcaggc gaaggacgtg   180
gagaccaagg agcagatcgc ctccaccgcc tccatctccg ctgccgacac ccagatcggc   240
gagctgatcg ccgaggccat ggacaaggtc ggcaaggaag gcgtcatcac cgtcgaggag   300
tcgcagacct tcggtctcga gctggagctc accgagggca tgcgcttcga caagggctac   360
atctccgcct acttcgccac cgacatggag cgcatggagg cggagctgga ggaccccta   420

<210> SEQ ID NO 13
<211> LENGTH: 420
<212> TYPE: DNA
<213> ORGANISM: Streptomyces anandii

<400> SEQUENCE: 13
aagaagacgg acgacgtcgc cggtgacggt acgaccaccg cgaccgtgct cgcccaggcc    60
ctggtccgcg agggcctgcg caacgtggcc gccggcgcca acccgatggc tctgaagcgc   120
ggtatcgaga aggccgtcga ggccgtctcc gccgccctgc tcgaccaggc caaggaggtc   180
gagaccaagg agcagatcgc ctccaccgcc tccatctccg ccgccgacac ccagatcggc   240
gagctcatcg ccgaggccat ggacaaggtc ggcaaggaag gcgtcatcac cgtcgaggag   300
tcgcagacct tcggtctgga gctcgagctc accgagggca tgcgcttcga caagggctac   360
atctccgcct acttcgccac cgacatggag cgcatggagg cgtcgctcga ggacccgtac   420

<210> SEQ ID NO 14
<211> LENGTH: 420
<212> TYPE: DNA
<213> ORGANISM: Streptomyces argenteolus

<400> SEQUENCE: 14
aagaagacgg acgacgtcgc cggtgacggc acgacgaccg cgaccgtcct ggcccaggcc    60
ctggtccgcg agggcctgcg caacgtcgcc gccggcgcca acccgatggc cctcaagcgc   120
ggtatcgaga aggccgtcga ggccgtctcc gccgccctgc tcgagcaggc caaggacgtg   180
gagaccaagg agcagatcgc ttcgaccgcc tccatctccg ccgccgacac ccagatcggc   240
gagctgatcg ccgaggccat ggacaaggtc ggcaaggaag gcgtcatcac cgtcgaggag   300
tcccagacct tcggtctgga gctggaactc accgagggta tgcgcttcga caagggctac   360
```
atctcggcgt acttcgcgac cgacatggag cgcatggaag ccgcgctcga cgacccgtac   420

<210> SEQ ID NO 15
<211> LENGTH: 420
<212> TYPE: DNA
<213> ORGANISM: Streptomyces bambergiensis

<400> SEQUENCE: 15
aagaagacgg acgacgtcgc cggtgacggt acgaccaccg cgaccgttct cgcccaggcc    60
ctggtcaagg agggcctgcg caacgtagcc gccggcgcca acccgatggc cctcaagcgc   120
ggtatcgaga aggccgtcga ggccgtctcc ggtgccctgc tggagcaggc gaaggacgtc   180
gagaccaagg agcagatcgc ctccacggcc tccatctccg ccgccgacac ccagatcggc   240
gagctcatcg ccgaggccat ggacaaggtc ggcaaggaag cgtcatcac cgtcgaggag    300 tcccagacct tcggtctgga gctcgagctc accgagggca tgcgcttcga caagggctac   360
atctcggcgt acttcgccac cgacatggag cgtatggagg cgtcgctcga cgacccgtac   420

<210> SEQ ID NO 16
<211> LENGTH: 420
<212> TYPE: DNA
<213> ORGANISM: Streptomyces capillispiralis

<400> SEQUENCE: 16
aagaagacgg acgacgtcgc cggtgacggt acgaccaccg cgaccgtcct cgcccaggcc    60
ctggtcaagg agggcctgcg caacgtcgcc gccggcgcca acccgatggc tctgaagcgc   120
ggtatcgaga aggccgtcga ggccgtctcc ggtgccctgc tggagcaggc gaaggatgtc   180
gagaccaagg agcagatcgc ctccacggcc tccatctccg ccgccgacac ccagatcggc   240
gagctcatcg ccgaggccat ggacaaggtc ggcaaggaag cgtcatcac cgtcgaggag    300 tcccagacct tcggtctgga gctggagctc accgagggta tgcgcttcga caagggctac   360
atctcggcgt acttcgccac cgacatggag cgtatggagg ccgtcctcga cgacccgtac   420

<210> SEQ ID NO 17
<211> LENGTH: 420
<212> TYPE: DNA
<213> ORGANISM: Streptomyces carpinensis

<400> SEQUENCE: 17
aagaagacgg acgacgtcgc cggtgacggc acgacgaccg cgaccgtcct ggcccaggcg    60
ctggtccgcg agggcctgcg caacgtggcc gcgggtgcca acccgatggc cctgaagcgc   120
ggcatcgaga aggccgtcga ggccgtctcg ggcgccctgc tcgaccaggc caaggaggtc   180
gagaccaagg agcagatcgc ctccacggcc tccatctccg ccgccgacac ccagatcggc   240
gagctgatcg ccgaggccat ggacaaggtc ggcaaggaag cgtcatcac cgtcgaggag    300 tcccagacct tcggtctgga gctggagctc accgagggta tgcgcttcga caagggctac   360
atctcggcgt acttcgcgac cgacatggag cgcatggagg cggcgctcga cgacccgtac   420

<210> SEQ ID NO 18
<211> LENGTH: 422
<212> TYPE: DNA
<213> ORGANISM: Streptomyces catenulae

<400> SEQUENCE: 18
aagaagacgg acgacgtcgc cggtgacggc acgacgaccg cgaccgtcct ggcccaggcg    60
ctggtccgcg agggcctccg taacgtcgcc gccggtgcca acccgatggc cctcaagcgg   120

-continued

```
ggcatcgaga ccgccgtcga ggccgtctcc gccgccctgc tggagcaggc caaggacgtg     180
gagaccaagg agcagatcgc ttcgaccgcc tccatctccg ccgccgacac ccagatcggc     240
gagctgatcg ccgaggccat ggacaaggtc ggcaaggaag cgtcatcac cgtcgaggag     300 tcccagacct tcggtctgga gctggagctc accgagggta tgcgcttcga caagggctac     360
atctcggcgt acttcgccac cgacatggag cgtatggagg cgtcgctcga cgacccgtac     420
at                                                                    422

<210> SEQ ID NO 19
<211> LENGTH: 420
<212> TYPE: DNA
<213> ORGANISM: Streptomyces cellulosae

<400> SEQUENCE: 19
aagaagacgg acgacgtcgc cggtgacggt acgaccacgg cgaccgttct cgcccaggcc      60
ctggtcaagg agggcctgcg caacgtcgcc gccggcgcca acccgatggc cctgaagcgc     120
ggtatcgaga aggccgtcga ggcggtctcc gccgccctgc tggagcaggc gaaggacgtg     180
gagaccaagg agcagatcgc ctccacggcc tccatctccg ccgccgacgt ccagatcggc     240
gagctcatcg ccgaggcgat ggacaaggtc ggcaaggaag cgtcatcac cgtcgaggag     300 tcccagacct tcggtctgga gctggagctc accgagggta tgcgcttcga caagggctac     360
atctcggcgt acttcgccac cgacatggag cgtatggagg ccgtcctcga cgacccgtac     420

<210> SEQ ID NO 20
<211> LENGTH: 420
<212> TYPE: DNA
<213> ORGANISM: Streptomyces chartreusis

<400> SEQUENCE: 20
aagaagacgg acgacgtcgc cggtgacggt acgaccaccg cgaccgttct cgcccaggcc      60
ctggtcaagg agggcctgcg caacgtagcc gccggcgcca acccgatggc cctcaagcgc     120
ggtatcgagc gtgccgtcga ggccgtctcc gccgccctgc tcgagcaggc caaggatgtc     180
gagaccaagg agcagatcgc ttccacggcc tccatctccg ccgccgacac ccagatcggc     240
gagctcatcg ccgaggcgat ggacaaggtc ggcaaggaag cgtcatcac cgtcgaggag     300 tcccagacct tcggtctgga gctggagctc accgagggta tgcgcttcga caagggctac     360
atctcggcgt acttcgccac cgacatggag cggatggagg cgtcgctcga cgacccgtac     420

<210> SEQ ID NO 21
<211> LENGTH: 420
<212> TYPE: DNA
<213> ORGANISM: Streptomyces chattanoogenesis

<400> SEQUENCE: 21
aagaagacgg actacgtcgc cggtgacggc acgacgaccg cgaccgtcct ggcccaggcc      60
ctggtccgcg agggcctgcg caacgttgcc gccggtgcca acccgatggc gctgaagcgc     120
ggtatcgaga aggccgtcga gtccgtctcc gccgccctgc tcgagcaggc gaaggatgtc     180
gagaccaagg agcagatcgc ttccaccgcc tccatctccg ccgccgacac ccagatcggt     240
gagctcatcg ccgaggcgat ggacaaggtc ggcaaggaag cgtcatcac cgtcgaggag     300 tcccagacct tcggtctgga gctggagctc accgagggta tgcgcttcga caagggctac     360
atctcggcgt acttcgcgac cgacatggag cgcatggagg cggtcctgga tgacccgtac     420
```

```
<210> SEQ ID NO 22
<211> LENGTH: 420
<212> TYPE: DNA
<213> ORGANISM: Streptomyces cinnamonensis

<400> SEQUENCE: 22
aagaagacgg acgacgtcgc cggcgacggt acgaccaccg ccaccgtcct ggcccaggcg      60
ctcgtccgcg agggcctgcg caacgtggcc gccggtgcca cccgatggc cctcaagcgt     120
ggtatcgaga aggccgtcga ggccgtctcc gccgccctgc tcgcccaggc caaggatgtc    180
gagaccaagg agcagatcgc ttccacggcc tccatctccg ccgccgacac ccagatcggc    240
gagctcatcg ccgaggccat ggacaaggtc ggcaaggaag gcgtcatcac cgtcgaggag    300
tcccagacct tcggtctgga gctggagctc accgagggta tgcgcttcga caagggctac    360
atctcggcgt acttcgccac cgacatggag cgcatggagt cgtccctcga cgacccgtac    420

<210> SEQ ID NO 23
<211> LENGTH: 420
<212> TYPE: DNA
<213> ORGANISM: Streptomyces cinereoruber

<400> SEQUENCE: 23
aagaagacgg acgacgtcgc cggtgacgga acgaccaccg cgaccgttct cgcccaggcg      60
ctggtccgcg agggccttcg caacgtcgcc gccggcgcca cccgatggc tctgaagcgc     120
ggtatcgaga aggccgtcga ggccgtctcc ggtgccctgc tcgagcaggc gaaggatgtc    180
gagaccaagg agcagatcgc ttcgacggcc tccatctccg ccgccgacac ccagatcggc    240
gagctcatcg ccgaggcgat ggacaaggtc ggcaaggaag gcgtcatcac cgtcgaggag    300
tcccagacct tcggtctgga gctggaactc accgagggca tgcgcttcga caagggctac    360
atctcggcgt acttcgccac cgacatggag cgtatggagg ccgtcctcga cgacccgtac    420

<210> SEQ ID NO 24
<211> LENGTH: 420
<212> TYPE: DNA
<213> ORGANISM: Streptomyces cirratus

<400> SEQUENCE: 24
aagaagacgg acgacgtcgc gggcgacggt acgaccaccg ccaccgtgct ggcccaggcg      60
ctcgtccgcg agggcctgcg caacgtggcc gccggcgcca cccgatggc cctcaagcgt     120
ggtatcgaga aggccgtcga ggccgtctcc gccgccctgc tcgcgcaggc caaggatgtc    180
gagaccaagg agcagatcgc ttcgacggcc tccatctccg ccgccgacac ccagatcggc    240
gagctcatcg ccgaggccat ggacaaggtc ggcaaggaag gcgtcatcac cgtcgaggag    300
tcccagacct tcggtctgga gctcgagctc accgagggca tgcgcttcga caagggctac    360
atctcggcgt acttcgccac cgacatggag cgtatggagg cgtcgctcga cgacccgtac    420

<210> SEQ ID NO 25
<211> LENGTH: 420
<212> TYPE: DNA
<213> ORGANISM: Streptomyces coeruleorubidus

<400> SEQUENCE: 25
aagaagacgg acgacgtcgc cggtgacggt acgaccaccg cgaccgttct cgcccaggcc      60
ctggtcaagg aaggcctgcg caacgtagcc gccggcgcca cccgatggc gctcaagcgc     120
ggtatcgagc gcgccgtcga ggccgtctcc gccgccctgc tggagcaggc gaaggacgtc    180
```

```
gagaccaagg agcagatcgc ctccacggcc tccatctccg ccgccgacac ccagatcggc    240
gagctcatcg ccgaggccat ggacaaggtc ggcaaggaag gcgtcatcac cgtcgaggag    300
tcccagacct tcggtctgga gctggagctc accgagggta tgcgcttcga caagggctac    360
atctcggcgt acttcgcgac cgacatggag cgtatggagg ccgtcctcga cgacccgtac    420

<210> SEQ ID NO 26
<211> LENGTH: 420
<212> TYPE: DNA
<213> ORGANISM: Streptomyces collinus

<400> SEQUENCE: 26
aagaagacgg acgacgtcgc cggtgacggt acgaccaccg cgaccgttct cgcccaggcc     60
ctggtcaagg agggtctgcg caacgtagcc gccggcgcca acccgatggc cctcaagcgc    120
ggtatcgagc gtgccgtcga ggccgtctcc gccgccctgc tggagcaggc gaaggacgtc    180
gagaccaagg agcagatcgc ctccacggcc tccatctccg ccgccgacac ccagatcggc    240
gagctcatcg ccgaggccat ggacaaggtc ggcaaggaag gcgtcatcac cgtcgaggag    300
tcccagacct tcggtctgga gctggagctc accgagggta tgcgcttcga caagggctac    360
atctcggcgt acttcgccac cgacatggag cgtatggagg ccgtcctcga cgacccgtac    420

<210> SEQ ID NO 27
<211> LENGTH: 420
<212> TYPE: DNA
<213> ORGANISM: Streptomyces corchorusii

<400> SEQUENCE: 27
aagaagacgg acgacgtcgc cggtgacggt acgaccaccg cgaccgtgct cgcccaggcc     60
ctggtcaagg aaggcctgcg caacgtcgcc gccggcgcca acccgatggc tctgaagcgc    120
ggtatcgaga aggccgtcga ggccgtctcc gccgccctgc tggagcaggc gaaggacgtc    180
gagaccaagg agcagatcgc ctccaccgcg tccatctccg ccgccgacac ccagatcggc    240
gagctgatcg ccgaggccat ggacaaggtc ggcaaggaag gcgtcatcac cgtcgaggag    300
tccaacacct tcggtcttga gctggagctc accgagggca tgcgcttcga caagggctac    360
atctccgcct acttcgcgac cgacatggag cgcatggagg cggtgctgga ggacccgtac    420

<210> SEQ ID NO 28
<211> LENGTH: 420
<212> TYPE: DNA
<213> ORGANISM: Streptomyces diastaticus

<400> SEQUENCE: 28
aagaagacgg acgacgtcgc cggtgacggt acgaccaccg cgaccgtcct cgcccaggcg     60
ctcgtccgtg agggcctgcg caacgtggcc gccggcgcca acccgatggc cctgaagcgc    120
ggcatcgaga aggccgtcga ggccgtctcc ggcgccctgc tcgagcaggc caaggacgtg    180
gagaccaagg agcagatcgc ctccaccgcc tccatctccg ccgcggacgt ccagatcggt    240
gagctcatcg ccgaggccat ggacaaggtc ggcaaggaag gcgtcatcac cgtcgaggag    300
tcccagacct tcggtctgga gctcgagctc accgaaggca tgcgcttcga caagggctac    360
atctcggcgt acttcgccac cgacatggag cgtatggagg cgtccctgga cgacccgtac    420

<210> SEQ ID NO 29
<211> LENGTH: 420
<212> TYPE: DNA
```

<213> ORGANISM: Streptomyces djakartensis

<400> SEQUENCE: 29

| | | | | | |
|---|---|---|---|---|---|
| aagaagacgg | acgacgtcgc | cggtgacggt | acgaccaccg | cgaccgtcct | cgcccaggcc | 60 |
| ctggtcaagg | aaggcctgcg | caacgtcgcc | gccggcgcca | acccgatggc | cctgaagcgc | 120 |
| ggtatcgagc | gcgccgtcga | ggccgtctcc | gccgccctgc | tggagcaggc | gaaggacgtc | 180 |
| gagaccaagg | agcagatcgc | ctccacggcc | tccatctccg | ccgccgacac | ccagatcggc | 240 |
| gagctcatcg | ccgaggccat | ggacaaggtc | ggcaaggaag | cgtcatcac | cgtcgaggag | 300 |
| tcccagacct | tcggtctgga | gctggagctc | accgagggta | tgcgcttcga | caagggctac | 360 |
| atctcggcgt | acttcgccac | cgacatggag | cgtatggagg | ccgtcctcga | cgacccgtac | 420 |

<210> SEQ ID NO 30
<211> LENGTH: 423
<212> TYPE: DNA
<213> ORGANISM: Streptomyces erumpens

<400> SEQUENCE: 30

| | | | | | |
|---|---|---|---|---|---|
| aagaagacgg | acgacgtcgc | cggtgacggc | acgaccaccg | cgaccgttct | ggcccaggcc | 60 |
| ctggtcacag | cggagggcct | gcgcaacgtc | gccgccggcg | ccaacccgat | ggccctgaag | 120 |
| cgcggtatcg | agaaggccgt | cgaggccgtc | tccgccgccc | tgctcgagca | ggccaaggac | 180 |
| gtggagacca | aggagcagat | cgcttccacc | gcctccatct | ccgccgccga | cacccagatc | 240 |
| ggcgagctga | tcgccgaggc | catggacaag | gtcggcaagg | aaggcgtcat | caccgtcgag | 300 |
| gagtcccaga | ccttcggtct | ggagctggaa | ctcaccgagg | gtatgcgctt | cgacaagggc | 360 |
| tacatctcgg | cgtactttgc | caccgacatg | gagcgcatgg | aggccgcgct | cgacgacccg | 420 |
| tac | | | | | | 423 |

<210> SEQ ID NO 31
<211> LENGTH: 420
<212> TYPE: DNA
<213> ORGANISM: Streptomyces fulvissimus

<400> SEQUENCE: 31

| | | | | | |
|---|---|---|---|---|---|
| aagaagacgg | acgacgtcgc | cggtgacggc | acgacgaccg | cgaccgtcct | cgcccaggcg | 60 |
| ctcgtcaagg | aaggcctgcg | caacgtcgcg | gccggcgcca | acccgatggc | cctcaagcgc | 120 |
| ggcatcgaga | aggccgtcga | ggccgtctcc | ggcgccctgc | tcgagcaggc | caaggacgtg | 180 |
| gagaccaagg | agcagatcgc | ttcgaccgcc | tccatctccg | ccgccgacac | ccagatcggc | 240 |
| gagctcatcg | ccgaggccat | ggacaaggtc | ggcaaggaag | cgtcatcac | cgtcgaggag | 300 |
| tcgcagacct | tcggtctgga | gctcgagctc | accgagggca | tgcgcttcga | caagggctac | 360 |
| atctcggcgt | acttcgccac | cgacatggag | cgtatggagg | cgtcgctcga | cgacccgtac | 420 |

<210> SEQ ID NO 32
<211> LENGTH: 420
<212> TYPE: DNA
<213> ORGANISM: Streptomyces galilaeus

<400> SEQUENCE: 32

| | | | | | |
|---|---|---|---|---|---|
| aagaagacgg | acgacgtcgc | cggtgacggt | acgaccaccg | cgaccgttct | cgcccaggcg | 60 |
| ctggtccgcg | agggcctgcg | caacgtggcg | gccggcgcca | acccgatggc | tctgaagcgc | 120 |
| ggcatcgaga | aggccgtcga | ggccgtctcc | ggtgccctcc | tcgagcaggc | gaaggatgtc | 180 |
| gagaccaagg | agcagatcgc | ttcgacggcc | tccatctccg | ccgccgacac | ccagatcggc | 240 |

```
gagctcatcg ccgaggcgat ggacaaggtc ggcaaggaag cgtcatcac ggtcgaggag    300 tcgcagacct tcggtctcga gctcgagctc accgagggca tgcgcttcga caagggctac    360
atctcggcgt acttcgcgac cgacatggag cgtatggagg ccgtcctcga cgacccgtac    420

<210> SEQ ID NO 33
<211> LENGTH: 420
<212> TYPE: DNA
<213> ORGANISM: Streptomyces griseochromogenes

<400> SEQUENCE: 33
aagaagacgg acgacgtcgc cggtgacggc acgacgaccg cgaccgtcct ggcccaggcc    60
ctggtcaagg aaggcctccg caacgtcgcc gccggcgcca acccgatggc tctgaagcgc    120
ggtatcgaga aggccgtcga ggccgtctcc gccgccctcc tcgagcaggc gaaggacgtc    180
gagaccaagg agcagatcgc ctccaccgcg tccatctccg ccgccgacac ccagatcggc    240
gagctgatcg ccgaggccat ggacaaggtc ggcaaggaag gcgtcatcac cgtcgaggag    300
agcaacacct tcggtctgga gctcgagctc accgagggca tgcgcttcga caagggctac    360
atctccgcct acttcgcgac cgacatggag cgcatggagg cggcgctcga ggacccgtac    420

<210> SEQ ID NO 34
<211> LENGTH: 420
<212> TYPE: DNA
<213> ORGANISM: Streptomyces griseolus

<400> SEQUENCE: 34
aagaagacgg acgacgtcgc cggcgacggt acgaccaccg ccaccgttct cgcccaggcg    60
ctcgtccgtg agggcctgcg caacgtcgcc gccggtgcca acccgatggc tctcaagcgt    120
ggcatcgaga aggccgtcga ggccgtctcc gccgccctgc tggagcaggc caaggacgtg    180
gagaccaagg agcagatcgc ttcgaccgcc tccatctccg ccgccgacac cgagatcggc    240
gccaagatcg ccgaggcgat ggacaaggtc ggcaaggaag gcgtcatcac cgtcgaggag    300
tcccagacct tcggtctgga gctggaactc accgagggta tgcgcttcga caagggctac    360
atctcggcgt acttcgccac cgacatggag cgtatggaga cgtcgttcga cgacccgtac    420

<210> SEQ ID NO 35
<211> LENGTH: 420
<212> TYPE: DNA
<213> ORGANISM: Streptomyces griseoviridis

<400> SEQUENCE: 35
aagaagacgg acgacgtcgc cggtgacggt acgaccaccg cgaccgtcct cgcccaggcc    60
ctggtcaagg agggcctgcg caacgtagcc gccggcgcca acccgatggc cctgaagcgc    120
ggtatcgaga aggccgtcga ggccgtctcc gccgccctgc tggagcaggc gaaggacgtc    180
gagaccaagg agcagatcgc ctccacggcc tccatctccg ccgccgacac ccagatcggc    240
gagctgatcg ccgaggccat ggacaaggtc ggcaaggaag gcgtcatcac cgtcgaggag    300
tcccagacct ttggtctgga gctggagctc accgagggta tgcgcttcga caagggctac    360
atctcggcgt acttcgccac cgacatggag cgtatggagg ccgtgctcga cgacccgtac    420

<210> SEQ ID NO 36
<211> LENGTH: 420
<212> TYPE: DNA
<213> ORGANISM: Streptomyces humiferus
```

<400> SEQUENCE: 36

```
aagaagacgg acgacgtcgc cggtgacggt acgaccaccg cgaccgttct cgcccaggcc      60
ctggtcaagg aaggcctgcg caacgtcgcg gccggcgcca acccgatggc cctgaagcgc     120
ggtatcgaga aggccgtcga ggccgtctcc gccgccctgc tcgagcaggc caaggacgtc     180
gagaccaagg agcagatcgc ctccacggcc tcgatctccg ccgccgacac ccagatcggc     240
gagctcatcg ccgaggccat ggacaaggtc ggcaaggaag cgtcatcac cgtcgaggag     300
tcccagacct tcggtctgga gctggagctc accgagggta tgcgcttcga caagggctac     360
atctcggcgt acttcgccac cgacatggag cgtatggagg cgtcgctcga cgacccgtac     420
```

<210> SEQ ID NO 37
<211> LENGTH: 420
<212> TYPE: DNA
<213> ORGANISM: Streptomyces hygroscopicus

<400> SEQUENCE: 37

```
aagaagacgg acgacgtcgc cggtgacggc acgacgaccg cgaccgtcct ggcccaggcc      60
ctggtccgcg agggcctgcg caacgtcgcc gccggcgcca acccgatggc cctcaagcgc     120
ggtatcgagc gtgccgtcga ggccgtctcc gccgccctgc tggagcaggc caaggacgtg     180
gagaccaagg agcagatcgc ttcgaccgcc tccatctccg ccgctgacac ccagatcggc     240
gagctcatcg ccgaggccat ggacaaggtc ggcaaggaag cgtcatcac cgtcgaggag     300
tcccagacct tcggtctgga gctggaactc accgagggta tgcgcttcga caagggctac     360
atctcggcgt acttcgccac cgacatggag cgtatggagg cgtcgctcga cgacccgtac     420
```

<210> SEQ ID NO 38
<211> LENGTH: 420
<212> TYPE: DNA
<213> ORGANISM: Streptomyces minutiscleroticus

<400> SEQUENCE: 38

```
aagaagacgg acgacgtcgc cggtgacggc acgacgaccg cgaccgtcct ggcccaggcg      60
ctggtccgcg agggcctgcg caacgtcgcc gccggcgcca acccgatggc cctgaagcgc     120
ggtatcgaga aggccgtcga ggccgtctcc ggtgccctgc tggagcaggc gaaggacgtc     180
gagaccaagg agcagatcgc ctccacggcc tccatctccg ccgccgacgt ccagatcggc     240
gagctcatcg ccgaggccat ggacaaggtc ggcaaggaag cgtcatcac cgtcgaggag     300
tcccagacct tcggtctgga gctggagctc accgagggta tgcgcttcga caagggctac     360
atctcggcgt acttcgccac cgacatggag cgtatggagg ccgtcctcga cgacccgtac     420
```

<210> SEQ ID NO 39
<211> LENGTH: 423
<212> TYPE: DNA
<213> ORGANISM: Streptomyces murinus

<400> SEQUENCE: 39

```
aagaagacgg acgacgtcgc cggtgacggt acgaccaccg cgaccgtcct cgcccaggcc      60
ctggtcacag cggaaggcct gcgcaacgtc gccgccggtg ccaacccgat ggccctgaag     120
cgcggtatcg agaaggccgt cgaggccgtc tccgccgccc tgctcgagca ggccaaggac     180
gtcgagacca aggagcagat cgcctccacc gcgtccatct ccgccgccga cacccagatc     240
ggcgagctga tcgccgaggc gatggacaag gtcggcaagg aaggcgtcat caccgtcgag     300
gagagcaaca ccttcggtct ggagcttgag ctcaccgagg gcatgcgctt cgacaagggc     360
```

```
tacatcttcg cctacttcgc caccgacatg gagcgcatgg aggcgtcgct cgacgacccg    420
tac                                                                  423

<210> SEQ ID NO 40
<211> LENGTH: 420
<212> TYPE: DNA
<213> ORGANISM: Streptomyces nodosus

<400> SEQUENCE: 40
aagaagacgg acgacgtcgc cggtgacggt acgaccaccg cgaccgtgct cgcccaggcg    60
ctggtccgcg agggcctgcg caacgtcgcc gccggtgcca acccgatggc cctgaagcgc   120
ggtatcgaga aggccgtcga ggccgtctcc accgccctgc tggagcaggc gaaggacgtc   180
gagaccaagg agcagatcgc ctccacggcc tccatctccg ccgccgacac ccagatcggc   240
gagctgatcg ccgaggccat ggacaaggtc ggcaaggaag cgtcatcac cgtcgaggag   300 tcgcagacct tcggtctcga gctcgagctc accgagggca tgcgcttcga caagggctac   360
atctcggcgt acttcgccac cgacatggag cgtatggagg ccgtcctcga cgacccgtac   420

<210> SEQ ID NO 41
<211> LENGTH: 420
<212> TYPE: DNA
<213> ORGANISM: Rhodococcus equi

<400> SEQUENCE: 41
aagaagaccg acgacgtcgc tggtgacggc accacgacgg ctacggtcct ggctcaggcg    60
ctcgtccgcg agggcctgcg caacgtcgct gccggcgcca acccgctggg tctgaagcgc   120
ggcatcgaga aggccgtcga ggccgtcacc gccaagctgc tcgacaccgc caaggaggtc   180
gagaccaagg agcagatcgc tgccaccgcc gggatctcgg cgggcgactc cacgatcggc   240
gagctcatcg ccgaggcgat ggacaaggtc ggcaaggaag cgtcatcac cgtcgaggag   300 tcgaactcct tcggcctgca gctcgagctc accgagggta tgcgcttcga caagggctac   360
atctcgctgt acttcgcgac cgacgccgag cgtcaggaag cggtcctcga ggatccgtac   420

<210> SEQ ID NO 42
<211> LENGTH: 420
<212> TYPE: DNA
<213> ORGANISM: Tsukamurella paurometabola

<400> SEQUENCE: 42
aagaagaccg acgacgtcgc gggcgacggc accaccaccg ccaccgttct ggcccaggcg    60
ctcgtgcgcg agggtctgcg caacatggct gcgggtgcga acccgctggg cctcaagcgg   120
ggcatcgaga aggccgtcga ggccgtgacc gagcacctgc tcaaggaggc caaggaggtc   180
gagaccaagg agcagatcgc tgctaccgcg gcatctcgg ccggcgaccc cgccatcggt    240
gagctcatcg ccgaggccat ggacaaggtc ggcaaggaag cgtcatcac cgtcgaggag   300 agcaacacct tcggtctcca gctggagctc accgagggca tgcgcttcga caagggcttc   360
atctccggct acttcgccac cgacgccgag cgtcaggagg ccgtgctcga ggacgcctac   420

<210> SEQ ID NO 43
<211> LENGTH: 420
<212> TYPE: DNA
<213> ORGANISM: Streptomyces scabiei

<400> SEQUENCE: 43
```

```
aagaagacgg acgacgtcgc cggtgacggt acgaccaccg cgaccgttct cgcccaggcg    60
ctcgtacgcg agggcctgcg caacgtcgcc gccggtgcca acccgatggc tctcaagcgc   120
ggcatcgaga aggccgtcga ggccgtctcc ggcgccctgc tggagcaggc gaaggatgtc   180
gagaccaagg agcagatcgc ttccacggcc tccatctccg ccgccgacac ccagatcggc   240
gagctcatcg ccgaggcgat ggacaaggtc ggcaaggaag gcgtcatcac cgtcgaggag   300
tcccagacct tcggtctgga gctggagctc accgagggta tgcgcttcga caagggctac   360
atctcggcgt acttcgccac cgacatggag cggatggagg cgtcgctcga cgacccgtac   420

<210> SEQ ID NO 44
<211> LENGTH: 420
<212> TYPE: DNA
<213> ORGANISM: Streptomyces scabiei

<400> SEQUENCE: 44
aagaagacgg acgacgtagc cggtgacggc acgacgaccg cgaccgtcct ggcccaggcg    60
ctggtccgcg agggcctgcg caacgtcgcc gccggcgcca acccgatggc cctgaagcgc   120
ggtatcgaga aggccgtcga ggccgtctcc ggtgcgctgc tcgaccaggc caaggaggtc   180
gagaccaagg agcagatcgc ctccacggcc tccatctccg ccgccgacac ccagatcggc   240
gagctcatcg ccgaggcgat ggacaaggtc ggcaaggaag gcgtcatcac cgtcgaggag   300
tcgcagacct tcgggcttga gcttgagctc accgagggca tgcgcttcga caagggctac   360
atctcggcgt acttcgcgac cgacatggag cgcatggagg ccgtgctcga ggaccccctac  420

<210> SEQ ID NO 45
<211> LENGTH: 420
<212> TYPE: DNA
<213> ORGANISM: Streptomyces scabiei

<400> SEQUENCE: 45
aagaagacgg acgacgtcgc cggtgacggt acgaccaccg cgaccgttct cgcccaggcg    60
ctcgtacgcg agggcctgcg caacgtcgcc gccggtgcca acccgatggc tctcaagcgc   120
ggcatcgaga aggccgtcga ggccgtctcc ggcgccctgc tggagcaggc gaaggatgtc   180
gagaccaagg agcagatcgc ttccacggcc tccatctccg ccgccgacac ccagatcggc   240
gagctcatcg ccgaggcgat ggacaaggtc ggcaaggaag gcgtcatcac cgtcgaggag   300
tcccagacct tcggtctgga gctggagctc accgagggta tgcgcttcga caagggctac   360
atctcggcgt acttcgccac cgacatggag cggatggagg cgtcgctcga cgacccgtac   420

<210> SEQ ID NO 46
<211> LENGTH: 420
<212> TYPE: DNA
<213> ORGANISM: Streptomyces scabiei

<400> SEQUENCE: 46
aagaagacgg acgacgtcgc cggcgacggt acgaccaccg ccaccgttct cgcccaggcg    60
ctcgtccgtg agggcctgcg caacgtcgcc gccggtgcca acccgatggc tctcaagcgt   120
ggcatcgaga aggccgtcga ggccgtctcc gccgccctgc tggagcaggc caaggacgtg   180
gagaccaagg agcagatcgc ttcgaccgcc tccatctccg ccgccgacac cgagatcggc   240
gccaagatcg ccgaggcgat ggacaaggtc ggcaaggaag gcgtcatcac cgtcgaggag   300
tcccagacct tcggtctgga gctggaactc accgagggta tgcgcttcga caagggctac   360
atctcggcgt acttcgccac cgacatggag cgtatggaga cgtcgttcga cgacccgtac   420
```

<210> SEQ ID NO 47
<211> LENGTH: 420
<212> TYPE: DNA
<213> ORGANISM: Streptomyces scabiei

<400> SEQUENCE: 47

| | | | | | | |
|---|---|---|---|---|---|---|
| aagaagacgg | acgacgtagc | cggtgacggc | acgacgaccg | cgaccgtcct | ggcccaggcc | 60 |
| ctggtgcgcg | agggtctgcg | caacgtggcc | gccggtgcca | acccgatggc | tctcaagcgc | 120 |
| ggcatcgaga | aggccgtcga | ggccgtctcc | ggcgccctgc | tggagcaggc | gaaggatgtc | 180 |
| gagaccaagg | agcagatcgc | ttccacggcc | tccatctccg | ccgccgacac | ccagatcggc | 240 |
| gagctcatcg | ccgaggcgat | ggacaaggtc | ggcaaggaag | gcgtcatcac | cgtcgaggag | 300 |
| tcccagacct | tcggtctgga | gctggagctc | accgagggta | tgcgcttcga | caagggctac | 360 |
| atctcggcgt | acttcgccac | cgacatggag | cgtatggagg | ccgtcctcga | cgacccgtac | 420 |

<210> SEQ ID NO 48
<211> LENGTH: 420
<212> TYPE: DNA
<213> ORGANISM: Streptomyces scabiei

<400> SEQUENCE: 48

| | | | | | | |
|---|---|---|---|---|---|---|
| aagaagacgg | acgacgtagc | cggtgacggc | acgacgaccg | cgaccgtcct | ggcccaggcc | 60 |
| ctggtgcgcg | agggtctgcg | caacgtggcc | gccggtgcca | acccgatggc | tctcaagcgc | 120 |
| ggcatcgaga | aggccgtcga | ggccgtctcc | ggcgccctgc | tggagcaggc | gaaggatgtc | 180 |
| gagaccaagg | agcagatcgc | ttccacggcc | tccatctccg | ccgccgacac | ccagatcggc | 240 |
| gagctcatcg | ccgaggcgat | ggacaaggtc | ggcaaggaag | gcgtcatcac | cgtcgaggag | 300 |
| tcccagacct | tcggtctgga | gctggagctc | accgagggta | tgcgcttcga | caagggctac | 360 |
| atctcggcgt | acttcgccac | cgacatggag | cgtatggagg | ccgtcctcga | cgacccgtac | 420 |

<210> SEQ ID NO 49
<211> LENGTH: 420
<212> TYPE: DNA
<213> ORGANISM: Streptomyces scabiei

<400> SEQUENCE: 49

| | | | | | | |
|---|---|---|---|---|---|---|
| aagaagacgg | acgacgtcgc | cggcgacggt | acgaccaccg | ccaccgttct | cgcccaggcg | 60 |
| ctcgtccgcg | agggcctgcg | caacgtcgcc | gcgggtgcca | acccgatggc | tctgaagcgt | 120 |
| ggcatcgaga | aggccgtcga | ggccgtctcc | ggcgctctgc | tggagcaggc | gaaggacgtg | 180 |
| gagaccaagg | agcagatcgc | ttcgacggcc | tccatctccg | ctgccgacac | cgagatcggc | 240 |
| gccaagatcg | ccgaggcgat | ggacaaggtc | ggcaaggaag | gcgtcatcac | cgtcgaggag | 300 |
| tcccagacct | tcggtctgga | gctggagctc | accgagggta | tgcgcttcga | caagggctac | 360 |
| atctcggcgt | acttcgccac | cgacatggag | cgtatggaga | cgtcgttcga | cgacccgtac | 420 |

<210> SEQ ID NO 50
<211> LENGTH: 420
<212> TYPE: DNA
<213> ORGANISM: Streptomyces acidiscabies

<400> SEQUENCE: 50

| | | | | | | |
|---|---|---|---|---|---|---|
| aagaagacgg | acgacgtagc | cggtgacggc | acgacgaccg | cgacggtcct | ggcccaggca | 60 |
| ctggtccgcg | agggcctccg | caacgtcgcc | gcaggcgcca | acccgatggc | cctgaagcgc | 120 |

```
ggcatcgaga aggccgtcga ggccgtctcc ggcgcgctcc tggagcaggc gaaggacgtc      180
gagaccaagg agcagatcgc ctccacggcc tccatctccg ccgccgacac gcagatcggc      240
gagctcatcg ccgaggcgat ggacaaggtc ggcaaggaag gcgtcatcac ggtcgaggag      300
tcgcagacct tcggcctgga gcttgagctc accgagggca tgcgcttcga caagggctac      360
atctcggcgt acttcgcgac cgacatggag cgcatggagt cgtccctgga cgacccgtac      420

<210> SEQ ID NO 51
<211> LENGTH: 420
<212> TYPE: DNA
<213> ORGANISM: Streptomyces turgidiscabies

<400> SEQUENCE: 51
aagaagacgg acgacgtagc cggtgacggc acgacgaccg cgaccgtcct ggcccaggcg       60
ctggtccgcg agggcctgcg caacgtggcc gcgggtgcga acccgatggc cctgaagcgc      120
ggcatcgaga aggccgtcga ggccgtctcc ggtgcgctgc tcgaccaggc gaaggaggtc      180
gagacgaagg agcagatcgc ttcgaccgcc tccatctccg ccgccgacac gcagatcggc      240
gagctcatcg ccgaggcgat ggacaaggtc ggcaaggaag gcgtcatcac cgtcgaggag      300
tcccagacct tcggtctgga gctggaactc accgagggta tgcgcttcga caagggctac      360
atctcggcgt acttcgcgac cgacatggag cgcatggagg cgtcgctcga ggaccccctac      420

<210> SEQ ID NO 52
<211> LENGTH: 420
<212> TYPE: DNA
<213> ORGANISM: Streptomyces turgidiscabies

<400> SEQUENCE: 52
aagaagacgg acgacgtagc cggtgacggc acgacgaccg cgaccgtcct ggcccaggcg       60
ctggtccgcg agggcctgcg caacgtggcc gcgggtgcga acccgatggc cctgaagcgc      120
ggcatcgaga aggccgtcga ggccgtctcc ggtgcgctgc tcgaccaggc gaaggaggtc      180
gagacgaagg agcagatcgc ttcgaccgcc tccatctccg ccgccgacac gcagatcggc      240
gagctcatcg ccgaggcgat ggacaaggtc ggcaaggaag gcgtcatcac cgtcgaggag      300
tcccagacct tcggtctgga gctggaactc accgagggta tgcgcttcga caagggctac      360
atctcggcgt acttcgcgac cgacatggag cgcatggagg cgtcgctcga ggaccccctac      420

<210> SEQ ID NO 53
<211> LENGTH: 420
<212> TYPE: DNA
<213> ORGANISM: Streptomyces turgidiscabies

<400> SEQUENCE: 53
aagaagacgg acgacgtagc cggtgacggc acgacgaccg cgaccgtcct ggcccaggcg       60
ctggtccgcg agggcctgcg caacgtggcc gcgggtgcga acccgatggc cctgaagcgc      120
ggcatcgaga aggccgtcga ggccgtctcc ggtgcgctgc tcgaccaggc gaaggaggtc      180
gagacgaagg agcagatcgc ttcgaccgcc tccatctccg ccgccgacac gcagatcggc      240
gagctcatcg ccgaggcgat ggacaaggtc ggcaaggaag gcgtcatcac cgtcgaggag      300
tcccagacct tcggtctgga gctggaactc accgagggta tgcgcttcga caagggctac      360
atctcggcgt acttcgcgac cgacatggag cgcatggagg cgtcgctcga ggaccccctac      420

<210> SEQ ID NO 54
<211> LENGTH: 420
```

```
<212> TYPE: DNA
<213> ORGANISM: Streptomyces turgidiscabies

<400> SEQUENCE: 54
aagaagacgg acgacgtagc cggtgacggc acgacgaccg cgaccgtcct ggcccaggcg      60
ctggtccgcg agggcctgcg caacgtggcc gcggtgcga acccgatggc cctgaagcgc     120
ggcatcgaga aggccgtcga ggccgtctcc ggtgcgctgc tcgaccaggc gaaggaggtc    180
gagacgaagg agcagatcgc ttcgaccgcc tccatctccg ccgccgacac gcagatcggc    240
gagctcatcg ccgaggcgat ggacaaggtc ggcaaggaag cgtcatcac cgtcgaggag     300
tcccagacct tcggtctgga gctggaactc accgagggta tgcgcttcga caagggctac   360
atctcggcgt acttcgcgac cgacatggag cgcatggagg cgtcgctcga ggacccctac   420

<210> SEQ ID NO 55
<211> LENGTH: 420
<212> TYPE: DNA
<213> ORGANISM: Streptomyces bottropensis

<400> SEQUENCE: 55
aagaagacgg acgacgtagc cggtgacggc acgacgaccg cgaccgtcct ggcccaggcc      60
ctggtgcgcg agggtctgcg caacgtggcc gccggcgcca acccgatggc cctcaagcgc    120
ggcatcgaga aggccgtcga ggccgtctcc ggcgccctgc tggagcaggc gaaggatgtc    180
gagaccaagg agcagatcgc ttccacggcc tccatctccg ccgccgacac ccagatcggc    240
gagctcatcg ccgaggcgat ggacaaggtc ggcaaggaag cgtcatcac cgtcgaggag     300
tcccagacct tcggtctgga gctggagctc accgagggta tgcgcttcga caagggctac   360
atctcggcgt acttcgccac cgacatggag cgtatggagg ccgtcctcga cgacccgtac    420

<210> SEQ ID NO 56
<211> LENGTH: 420
<212> TYPE: DNA
<213> ORGANISM: Streptomyces diastatochromogenes

<400> SEQUENCE: 56
aagaagacgg acgacgtcgc cggtgacggt acgaccaccg cgaccgttct cgcccaggcc      60
ctggtcaagg aaggcctgcg caacgtagcc gccggcgcca acccgatggc cctcaagcgc    120
ggcatcgaga aggccgtcga ggccgtctcc ggtgcgctgc tcgaccaggc caaggaggtc   180
gagaccaagg agcagatcgc ctccacggcc tccatctccg ccgccgacac ccagatcggc    240
gagctgatcg ccgaggccat ggacaaggtc ggcaaggaag cgtcatcac cgtcgaggag     300
tcgcagacct tcggtctgga gcttgagctc accgagggca tgcgcttcga caagggctac   360
atctcggcgt acttcgcgac cgacatggag cgcatggagg cggtcctgga ggacccctac   420

<210> SEQ ID NO 57
<211> LENGTH: 420
<212> TYPE: DNA
<213> ORGANISM: Streptomyces neyagawaensis

<400> SEQUENCE: 57
aagaagacgg acgacgtcgc cggtgacggt acgaccaccg cgaccgtcct cgcccaggcg      60
ctcgtacgcg agggcctgcg caacgtcgcc gccggtgcca acccgatggc cctgaagcgc    120
ggtatcgaga aggccgtcga ggccgtctcc ggtgcgctgc tcgaccaggc caaggaggtc   180
gagaccaagg agcagatcgc ctccacggcc tccatctccg ccgccgacac ccagatcggc    240
```

```
gagctgatcg ccgaggccat ggacaaggtc ggcaaggaag cgtcatcac cgtcgaggag      300 tcgcagacct tcggtctgga gctcgagctc accgagggca tgcgcttcga caagggctac    360
atctcggcgt acttcgccac cgacatggag cgcatggagg cggtgctcga ggacccctac    420
```

<210> SEQ ID NO 58
<211> LENGTH: 420
<212> TYPE: DNA
<213> ORGANISM: Streptomyces scabiei

<400> SEQUENCE: 58

```
aagaagacgg acgacgtcgc cggtgacggt acgaccaccg cgaccgttct cgcccaggcg      60
ctcgtacgcg agggcctgcg caacgtcgcc gccggtgcca acccgatggc tctcaagcgc    120
ggcatcgaga aggccgtcga ggccgtctcc ggcgccctgc tggagcaggc gaaggatgtc    180
gagaccaagg agcagatcgc ttccacggcc tccatctccg ccgccgacac ccagatcggc    240
gagctcatcg ccgaggcgat ggacaaggtc ggcaaggaag cgtcatcac cgtcgaggag    300 tcccagacct tcggtctgga gctggagctc accgagggta tgcgcttcga caagggctac    360
atctcggcgt acttcgccac cgacatggag cgtatggagg ccgtcctcga cgacccgtac    420
```

<210> SEQ ID NO 59
<211> LENGTH: 420
<212> TYPE: DNA
<213> ORGANISM: Streptomyces scabiei

<400> SEQUENCE: 59

```
aagaagacgg acgacgtagc cggtgacggc acgacgaccg cgaccgtcct ggcccaggcg      60
ctggtccgcg aaggcctgcg caacgtcgcc gccggtgcca acccgatggc cctgaagcgc    120
ggtatcgaga aggccgtcga ggccgtctcc ggtgcgctgc tcgaccaggc caaggaggtc    180
gagaccaagg agcagatcgc ctccacggcc tccatctccg ccgccgacac ccagatcggc    240
gagctcatcg ccgaggcgat ggacaaggtc ggcaaggaag cgtcatcac cgtcgaggag    300 tcgcagacct tcgggctcga gcttgagctc accgagggca tgcgcttcga caagggctac    360
atctcggcgt acttcgcgac cgacatggag cgcatggagg ccgtgctcga ggacccctac    420
```

<210> SEQ ID NO 60
<211> LENGTH: 420
<212> TYPE: DNA
<213> ORGANISM: Streptomyces acidiscabies

<400> SEQUENCE: 60

```
aagaagacgg acgacgtagc cggcgacggc acgacgaccg cgacggtcct ggcccaggcc      60
ctggtccgcg agggcctccg caacgtcgcc gccggcgcca acccgatggc cctcaagcgc    120
ggcatcgaga aggccgtcga ggccgtctcc ggcgcgctcc tggagcaggc gaaggacgtc    180
gagaccaagg agcagatcgc ctccacggcc tccatctccg ccgccgacac ccagatcggc    240
gagctcatcg ccgaggcgat ggacaaggtc ggcaaggaag cgtcatcac cgtcgaggag    300 tcccagacct tcggtctgga gctggaactc accgagggca tgcgcttcga caagggctac    360
atctcggcct acttcgcgac cgacatggag cgtatggagg cgtccctgga cgacccgtac    420
```

<210> SEQ ID NO 61
<211> LENGTH: 420
<212> TYPE: DNA
<213> ORGANISM: Streptomyces acidiscabies

<400> SEQUENCE: 61

```
aagaagacgg acgacgtcgc cggtgacggc acgacgaccg cgacggtcct ggcccaggca        60
ctggtccgcg agggcctccg caacgtcgcc gccggcgcca acccgatggc cctgaagcgc       120
ggcatcgaga aggccgtcga ggccgtctcc ggcgccctgc tggagcaggc gaaggacgtc       180
gagaccaagg agcagatcgc ctccacggcc tccatctccg ccgccgacac ccagatcggc       240
gagctcatcg ccgaggcgat ggacaaggtc ggcaaggaag gcgtcatcac ggtcgaggag       300
tcccagacct tcggtctgga gctggagctc accgagggca tgcgcttcga caagggctac       360
atctcggcgt acttcgcgac cgacatggag cgtatggagg cgtccctgga cgacccgtac       420
```